US006858712B1

(12) United States Patent
Chang et al.

(10) Patent No.: US 6,858,712 B1
(45) Date of Patent: Feb. 22, 2005

(54) CLONING AND EXPRESSION OF HTLV-III DNA

(75) Inventors: Nancy T. Chang, Houston, TX (US); Robert C. Gallo, Bethesda, MD (US); Flossie Wong-Staal, San Diego, CA (US)

(73) Assignees: The United States of America as represented by the Department of Health and Human Services, Washington, DC (US); Centocor, Inc., Malvern, PA (US)

( * ) Notice: Subject to any disclaimer, the term of this patent is extended or adjusted under 35 U.S.C. 154(b) by 0 days.

(21) Appl. No.: 08/463,209

(22) Filed: Jun. 5, 1995

Related U.S. Application Data

(60) Division of application No. 06/693,866, filed on Jan. 23, 1985, which is a continuation-in-part of application No. 06/659,339, filed on Oct. 10, 1984, now abandoned, which is a continuation-in-part of application No. 06/643,306, filed on Aug. 22, 1984, now abandoned.

(51) Int. Cl.[7] .......................... C07H 21/02; C12Q 1/68; C12P 19/34
(52) U.S. Cl. .................. 536/23.1; 536/24.3; 536/24.31; 536/24.33; 435/6; 435/91.2
(58) Field of Search ........................ 435/6, 5; 536/23.1, 536/23.72, 25.32; 424/1.73

(56) References Cited

U.S. PATENT DOCUMENTS

| | | | |
|---|---|---|---|
| 4,520,113 A | 5/1985 | Gallo | 435/5 |
| 4,689,398 A | 8/1987 | Wu | 530/327 |
| 4,708,818 A | 11/1987 | Montagnier | 435/5 |
| 4,716,102 A | 12/1987 | Levy | 435/5 |
| 4,725,669 A | 2/1988 | Essex | 530/322 |
| 5,135,864 A | 8/1992 | Montagnier | 435/235.1 |

OTHER PUBLICATIONS

Lehninger, Biochemistry (Worth Publishers, Inc., 1975, New York, NY), p 313.*
Condra et al, "Genetic correlates of in vivo viral resistance to Indinavir, a human immunodeficiency virus type 1 protease inhibitor", Journal of Virology (1996) 70(12):8270–8276.*
Anilonis, A., et al., Structure of the glycoprotein gene in rabies virus. Nature 294: 275–278 (1981).
Arya, S.K., et al., Homology of genome of AIDS–associated virus with genomes of human T–cell leukemia viruses. Science 225:927–929 (1984).
Ghrayeb, J., et al., Secretion cloning vectors in Escherichia coli, EMBO J., 3:2437–2442 (1984).
Gray, M.R., et al., Open reading frame cloning: Identification, cloning, and expression of open reading frame DNA, Proc. Nat'l Acad. Sci. USA 79: 6598–6602 (1982).
Hahn, B.H., et al. Molecular cloning and characterization of the HTLV–III virus associated with AIDS. Nature 312:166–169 (1984).

Kalyanaraman, V.S., et al., Antibodies to the core protein of lymphadenopathy associated virus (LAV) in patients with AIDS. Science 225:321–323 (1984).
Kiyokawa, T., et al., Envelope proteins of human T–cell leukemia virus. Proc.Nat'l.Acad.Sci.USA 81 6202–6206 (1984).
Montagnier, L., et al., Adaptation of Lymphadenopathy associated virus (LAV) to replication in EBV–transformed B lymphoblastoid cell lines. Science, 225: 63–66 (1984).
Ratner, L., et al. Complete nucleotide sequence of the AIDS virus, HTLV–III. Nature 313:277–284 (1985).
Ruther, U., et al., Easy identification of cDNA clones, EMBO J., 2:1791–1794 (1983).
Safai, B., et al., Seroepidemiological studies of human T–lymphotropic retrovirus type III in acquired immunodeficiency syndrome. The Lancet, 1438–1440 (1984).
Sarngadharan, M.G., et al., Antibodies reactive with human T–lymphotropic retroviruses (HTLV–III) in serum of patients with AIDS. Science 224:506–508 (1984).
Schupbach, J., et al., Serological Analysis of a subgroup of human T–Lymphotropic retroviruses (HTLV–III) associated with AIDS. Science 224:503–505 (1984).
Seiki, M., et al., Human adult T–cell leukemia virus: Complete nucleotide sequence of the provirus genome integrated in leukemia cell DNA. Proc Nat'l Acad Sci USA 80: 3618–22 (1983).
Shaw, G.M., et al. Molecular characterization of human T–cell leukemia (lymphotorpic) virus type III in the acquired immune deficiency syndrome. Science 226: 1165–1171 (1984).
Suggs, S. V., et al., Use of synthetic oligonucleotides as hybridization probes: Isolation of cloned cDNA sequences for human $\beta_2$–microglobulin. Proc Nat'l Acad Sci USA 78:6613–17 (1981).
Weinstock, G.M., et al., Open reading frame expression vectors: A general method for antigen production in Escherichia coli using protein fusions to β–galactosidase. Proc Nat'l Acad Sci USA 80: 4432–36 (1983).
Chiron Corporation v. Abbott Laboratories, 902 F.Supp. 1103, 1130 (N.D.Cal. 1995).
Settlement Agreement and Stipulation for Dismissal and Order dated Aug. 27, 1996.
Declaration of John A.T. Young, Ph.D. (Declaration Exhibit 1 LUCIW, Interference No. 103,659).
Expert Report of Robin A. Weiss, Ph.D., dated Apr. 17, 1995 (Declaration Exhibit 46 LUCIW, Interference No. 103,659).
Declaration of Robin A. Weiss, Ph.D., dated Feb. 15, 1996 (Declaration Exhibit 2 LUCIW, Interference No. 103,659).
Declaration of William Robinson, M.D. (Declaration Exhibit 3 LUCIW, Interference No. 103,659).

* cited by examiner

Primary Examiner—Jeffrey Fredman
(74) Attorney, Agent, or Firm—Leydig, Voit & Mayer, LTD

(57) ABSTRACT

The determination of the nucleotide sequence of HTLV-III DNA; identification, isolation and expression of HTLV-III sequences which encode immunoreactive polypeptides by recombinant DNA methods and production of viral RNA are disclosed. Such polypeptides can be employed in immunoassays to detect HTLV-III.

16 Claims, 27 Drawing Sheets

FIG. 3

| CLONE | | NUCLEOTIDE POSITION | AMINO ACID RESIDUE |
|---|---|---|---|

```
                          ├──U3
                          IR
BM10    TGGAAGGGCTAATTCACTCCAACGAAGACAAGA                                   -420
BM8     --------------------------------

(BamHI)
BM10    TATCCTTGATCTGTGGATCTACCACACACAAGGCTACTTCCCTGATTAGCAGAACTACACACCAGGGCCAGGAT   -345
BM8     ---------------C-------------------------------------------------AG-

BM10    CAGATATCCACTGACCTTTGGATGGTGCTACAAGCTAGTACCAGTTGAGCCAGAGAAGTTAGAGAAGCCAACAA   -270
BM8     --------------------------------G------------------------------T---

BM10    AGGAGAGAACACCAGTTGTTACACCCTGTGAGCCTGCATGGAATGATGACCCGGAGAGAGAAGTGTTAGAGTG    -195
BM8     ---------------------------------------T----------------------------

BM10    GAGGTTTGACAGCCGCCTAGCATTTCATCACATGGCCCGAGAGCTGCATCCGGAGTACTTCAAGAACTGCTGACA   -120
BM8     -----------------------------------------------------------------T--

BM10    TCGAGCTTGCTACAAGGGACTTTCCGCTGGGGACTTTCCAGGGAGGCGTGGCCTGGGCGTGGGGAGTGGCG      -45
BM8     ----------------------------------------------------------------

TATA    PvuII                                U3 ┐
              BOX                                              │
BM10    AGCCCTCAGATCCTGCATATAAGCAGCTGCTTTTTGCCTGTACT                                 -1
BM8     --------------------------------------------

┴─R         BglII      SstI
BM10    GGGTCTCTCTGGTTAGACCAGATCTGAGCCTGGGAGCTC
BM8     ---------------------------------------

HindIII    R──────────U5─────────
BM10    TAAAGCTTGCCTTGAGTGCTTCAAGTAGTGTGTGCCCGTCTGTTGTGTGACTCTGGTAACTAGAGATCCCTCAGA   75
BM8     ------------------------------------------------------------
                                            U5┬┐
                                              IR
MXB2    TCTGGCTAACTAGGGAACCCACTGCTTAAGCCTCAA                                         150

┬────leader sequence
MXB2    CCCTTTAGTCAGTGTGGAAAATCTCTAGCAGTGGCGCCCGAACAGGGACCTGAAAGGGAAAGGGAAACCA       221
                                         ┴──tRNA-lysine
```

FIG. 3 (Continued)

```
BH10  GAGCTCTCTCGACGCAGGACTCGGCTTGCTGAAGCGCGCACGCAGGGGCGAGGGGCGGCGACTGGTGAGTACG                    296
BH5   ------------------------------------------------------------------------
                                    Leader sequence ──┬── GAG p17
BH10  CCAAAAATTTTGACTAGCGGAGGCTAGAAGGAGAGAGATGGGTGCGAGAGCGTCAGTATTAAGCGGGGGAGATT                   371
                                           MetGlyAlaArgAlaSerValLeuSerGlyGlyGluLeu
BH5   ------------------------------------------------------------------------

BH10  AGATCGATGGGAAAAATTCGGTTAAGGCCAGGGGGAAAGAAAAAATATAAATTAAAACATATAGTATGGGCAAG                   446
      AspArgTrpGluLysIleArgLeuArgProGlyLeuLysLysTyrLysLeuLysHisIleValTrpAlaSer
BH5   ------------------------------------------------------------------------

BH10  CAGGGAGCTAGAACGATTCGCAGTTAATCCTGGCCTGTTAGAAACATCAGAAGGCTGTAGACAAATACTGGGACA                  521
      ArgGluLeuGluArgPheAlaValAsnProGlyLeuLeuGluThrSerGluGlyCysArgGlnIleLeuGlyGln
BH5   ------------------------------------------------------------------------

BH10  GCTACAACCATCCCTTCAGACACAGGATCAGAAGAACTTAGATCATTATATAATACAGTAGCAACCCTCTATTGTGT               596
      LeuGlnProSerLeuGlnThrGlySerGluLeuLeuArgSerLeuTyrAsnThrValAlaThrLeuTyrCysVal
BH5   ------------------------------------------------------------------------
                                       Hind III
BH10  GCATCAAAGGATAGAGATAAAAGACACCAAGAAGCTTTAGACAAGATAGAGGAAGAGCAAAACAAAAGTAAGAA                  671
      HisGlnArgIleGluIleLysAspThrLysGluAlaLeuAspLysIleGluGluGluGlnAsnLysSerLysLys
BH5   ------------------------------------------------------------------------
```

```
BM10  ACCAAAAGAACCTTTAGAGACTATGTAGACCGGTTCTATAAAACTCTAAGACCGAGCAAGCTTCACAGGAGGT  1271
                                                                    Hind III
      ProLysGluProPheArgAspTyrValAspArgPheTyrLysThrLeuArgAlaGluArgGlnAlaSerGlnGluVal
BM5   -----G-----C---------------------------------------------------------A---           313

BM10  AAAAATTGGATGACAGAGAAACCTTGTTGGTCCAAAATGCGAACCCAGATTGTAAGACTATTTTAAAGCATTGGG  1346
                                                                    Aha III
      LysAsnTrpMetThrGluThrLeuLeuValGlnAsnAlaAsnProAspCysLysThrIleLeuLysThrIleLeuLysAlaLeuGly
BM5   -------------------------------------------------------------------------------        338

BM10  ACCAGCGGGCTACACTAGAAGAAATGATGACAGCATGTCAGGGGAGTAGGAGGACCCGGCCATAAGGCAAGAGTTT  1421
      ProAlaAlaThrLeuGluGluMetMetThrAlaCysGlnGlyValGlyProGlyHisLysLysAlaArgValLeu
BM5   -----T--A--------------------------------------------------------------------          363
         SerThr

BM10  GGCTGAAGCAATGAGCCAAGTAACAAATACAGCTACCATAATGATGCAGAGAGCCAATTTTAGGAACCAAAGAAA  1496
      AlaGluAlaMetSerGlnValThrAsnThrAlaThrIleMetMetGlnArgAlaAsnPheArgAsnGlnArgLys
BM5   -------------A------------------------------------------------------------------       388

BM10  GATGGTTAAGTGTTTCAATTGTGGCAAAGAATTGCAGGCACACAGCCAGAAATTGCAGGGGCCCCTAGGAAAAAGGGCTG  1571
      MetValLysCysPheAsnCysGlyLysGluGlyHisGlnGlyHisThrAlaArgAsnCysArgAlaProArgLysGlyCys
BM5   A--T-------------------------------------------------T--A-----------A---GA------       413
         Ile                                              Lys
                                                                    Pol
                                                                    Bgl II
BM10  TTGGAAATGTGGAAAGGAAGGACACACCAAATGAAAGATTGTACTGAGAGACAGGCTAATTTTTAGGGAAGATCTG  1646
      TrpLysCysGlyLysGluGlyHisGlnMetLysAspCysThrGluArgGlnAlaAsnPheLeuGlyLysIleTrp
                                                                    PhePheArgGluAsp Leu
BM5   -------------------Direct Repeat-------------------------------------------------      438
                                                                                              6

BM10  GCCTTCCTACAAGGGAAGGCCAGGGAATTTCTTCAGAGACCAGGACCAACCAGCCCCACCATTTCTTCAGAG  1721
      ProSerTyrLysGlyArgProGlyAsnPheLeuGlnSerArgProGluProThrAlaProProPheLeuGlnSer
      AlaPheLeuGlnGlyLysLysAlaArgGlnThrArgArgAlaAsnSerProThrIleSerSerGlu
BM5   -------------------Direct Repeat---------------------------------------                 463
                                                                                              31
```

FIG. 3 (Continued)

```
                Repeat
BM10  CAGACCAGAGCCAACAGCCCCACCAGAGAGAGCTTCAGGTCTGGGGTAGAGACAACAACTCCCCCTCAGAAGCA  1796
       ArgPr GluProThrAlaProProGluGluSerPheArgSerGlyValGluThrThrProProGlnLysGln  488
                                                                                  56
BM5   GlnThrArgAlaAsnSerProThrArgArgGluLeuGlnValTrpGlyArgAspAsnSerProSerGluAla
      ------------------------------------T----------------------------T--------

BM10  GGAGCCCGATAGACAAGGAACTGTATCCTTTAACTTCCCTCAGATCACTCTTTGGCAACGACCCCTCGTCACAATA  1871
       GluPr IleAspLysGluLeuTyrProLeuThrSerLeuArgSerLeuPheGlyAsnAspProSerSerGln    512
                                         Ser                                      81
                                         Leu
                                        GAG p15
BM5   GlyAlaAspArgGlnGlyThrValSerPheAsnPheProGlnIleThrLeuTrpGlnArgProLeuValThrIle
      -----------------------------------------------------------------------------

BM10  AAGATAGGGGGCAACTAAAGGAAGCTCTATTAGATACAGGAGCAGATGATACAGTATTAGAAGAAATGAGTTTG  1946
       LysIleGlyGlyGlnLeuLysGluAlaLeuLeuAspThrGlyAlaAspAspThrValLeuGluGluMetSerLeu 106
BM5   
      -----------------------------------------------------------------------------

BM10  CCAGGAAGATGGAAACAAAATGATAGGGGGAATTGGAGGTTTTATCAAAGTAAGACAGTATGATCAGATACTC  2021
       ProGlyArgTrpLysGlnAsnAspArgGlyIleGlyGlyPheIleLysValArgGlnTyrAspGlnIleLeu    131
BM5   
      -----------------------------------------------------------------------------

BM10  ATAGAAATCTGTGGACATAAAGCTATAGGTACAGTATTAGTAGGACCTACACCTGTCAACATAATTGGAAGAAAT  2096
       IleGluIleCysGlyHisLysAlaIleGlyThrValLeuValGlyProThrProValAsnIleIleGlyArgAsn 156
                 Aha III
BM5   
      -----------------------------------------------------------------------------

BM10  CTGTTGACTCAGATTGGTTGCACTTTAAATTTTCCCATTAGCCCTATTGAGACTGTACCAGTAAAATTAAAGCCA  2171
       LeuLeuThrGlnIleGlyCysThrLeuAsnPheProIleSerProIleGluThrValProValLysLeuLysPro 181
BM5   
      --------------------------------A--------------T----------A------------------
```

```
BM10  GGAATGGATGGCCCAAAAGTTAAACAATGGCCATTGACAGAAGAAAATAAAAGCATTAGTAGAAATTTGTACA  2246
      GlyMetAspGlyProLysValLysGlnTrpProLeuThrGluGluLysIleLysAlaLeuValGluIleCysThr
BM5   -----------------------------------------------------------------------------

BM10  GAAATGGAAAAGGAAGGGAAAATTTCAAAAATTTGGGCCTGAGAATCCATACAATACTCCAGTATTTGCCATAAAG  2321
      GluMetGluLysGluGlyLysIleSerLysIleGlyLeuGluAsnProTyrAsnThrProValPheAlaIleLys
BM5   ---------------------------------------------A-------------------------------

BM10  AAAAAGACAGTACTAAATGGAGAAAATTAGTAGATTTCAGAGAACTTAATAAGAACTCAAGACTTCTGGGAA  2396
      LysLysAspSerThrLysTrpArgLysLeuValAspPheArgGluLeuAsnLysArgThrGlnAspPheTrpGlu
BM5   -----------------------------------G----------------------------------------
                                         Arg

BM10  GTTCAATTAGGAATACCACATCCCGCAGGGTTAAAAAGAAAATCACTAACAGTACTGGATGTGGGTGATGCA  2471
      ValGlnLeuGlyIleProHisProAlaGlyLeuLysLysLysSerValThrValLeuAspValGlyAspAla
BM5   ------------G---------------------------------------------------------------

BM10  TATTTTCAGTTCCCTTAGATGAAGACTTCAGGAAGTATACTGCATTACCATAGTATAAACAATGAGACA  2546
      TyrPheSerValProLeuAspGluAspPheArgLysTyrThrAlaPheThrIleProSerIleAsnGluThr
BM5   ------------------------------------------------T---------------------------

BM10  CCAGGGATTAGATACAATGTGCTTCCACAGGGATGGAAAGGATCACCAGCAATATTCCAAAGTAGCATG  2621
      ProGlyIleArgTyrGlnTyrAsnValLeuProGlnGlyTrpLysGlySerProAlaIlePheGlnSerSerMet
BM5   ------G-G--------------------------------------------------------------------
            SerGly
            Aha III

BM10  ACAAAATCTTAGAGCCTTTAAAAACAAAATCCAGACATAGTTATCTCAATACATGGATGATTTGTATGTA  2696
      ThrLysIleLeuGluProPheLysLysGlnAsnProAspIleValIleIleTyrGlnTyrMetAspAspLeuTyrVal
BM5   --------------G--------------------------------------T-----------------------
                  Arg
```

FIG. 3 (Continued)

```
BM10    GGATCTGACTTAGAAATAGGGCAGCAGATAGAACAAAAATAGAGGAGCTGAGACAACATCTGTTGAGGTGGGACTT    2771
        GlySerAspLeuGluIleGlyGlnGlnHisArgThrLysIleGluGluLeuArgGlnHisLeuLeuArgTrpGlyLeu
BM5     ---------------------------------------------T-----------------------------    381
                                                      Phe

BM10    ACCACCAGACACAAAAACATCAGAAAGAACCTCCATTCCTTTGGATGGGTTATGAACTCCATCCTGATAAATGG    2846
        ThrThrProAspLysHisGlnLysGluProPheLeuProProMetGlyTyrGluLeuHisProAspLysTrp
BM5     --------------------------------------------------------------------------    406

PvuII
BM10    ACAGTACAGCCTATAGTGCTGCCAGAAAAAGACAGCTGGACTGTCAATGACATACAGAAGTTAGTGGGGAAATTG    2921
        ThrValGlnProIleValLeuProGluLysAspSerTrpThrValAsnAspIleGlnLysLeuValGlyLysLeu
BM5     -------------------------------------------------------------A------------    431
              Ile

BM10    AATTGGGCAAGTCAGATTTACCCAGGGATTAAAGTAAGGCAATTAAGTGTAAACTCCTTAGAGGAACCAAGCACTA    2996
        AsnTrpAlaSerGlnIleTyrProGlyIleLysValArgGlnLeuCysLysLeuLeuArgGlyThrLysAlaLeu
BM5     --------------------T-----------------------------------------------------    456

BM10    ACAGAAGTAATACCACTAACAGAAGAGCAGAACTGGCAGAAAACAGAGATTCTAAAGAACCAGTAGATTCTAAAGAACCAGTA    3071
        ThrGluValIleProLeuThrGluGluAlaGluLeuAsnArgGluIleLeuLysGluProVal
BM5     --------------------------------------------------------------------------    481

BM10    CATGGAGTGTATTATGACCCATCAAAAGACTTAATAGCAGAAATACAGAAGCAGGGGCAAGGCCAATGGACATAT    3146
        HisGlyValTyrTyrAspProSerLysAspLeuIleAlaGluIleGlnLysGlnGlyGlnTrpThrTyr
BM5     --------------------------------------------------------------------------    506

AhaIII
BM10    CAAATTTATCAAGAGCCATTTAAAATCTGAAAATCTGAAAATATGCAAGAATATGCCACACTAATGAT    3221
        GlnIleTyrGlnGluProPheLysAsnLeuLysThrGlyLysTyrAlaArgMetArgGlyAlaHisThrAsnAsp
BM5     --------------------------------------------------------------------------    531
                                                                      AhaIII
BM10    GTAAAACAATTAACAGAGGCAGTGCAAAAAATAACCACAGAAAGACATAGTAATATGGGAAAGACTCCTAAATTT    3296
        ValLysGlnLeuThrGluAlaValGlnLysIleThrThrGluSerIleValIleTrpGlyLysThrProLysPhe
BM5     --------------------------------------------------------------------------    556
```

FIG. 3 (Continued)

```
BM10  AACTACCCATACAAAGGAAACATGGGAAACAGAGTATTGGCAAGCCACCTGGATTCCTGAGTGG    3371
      LysLeuProIleGlnLysGluThrTrpGluThrTrpGlnAlaThrTrpIleProGluTrp
BM5   ------------------A----------------------------------------        581

BM10  GAGTTTGTTAATACCCCTCCTTTAGTGAATTATGGTGAGAAAGAACCCATAGTAGGAGCAGAAACC  3446
      GluPheValAsnThrProProLeuValLysLeuTrpIleTyrGlnLeuGluLysGluAlaGluThr
BM5   ----------------------------------------------------------------  606
                                                               Lys I

BM10  TTCTATGTAGATGGGGCAGCTAACAGGGAGACTAAATTAGGAAAAGCAGGATATGTTACTAACAAAGGAAGACAA  3521
      PheTyrValAspGlyAlaAlaAsnArgGluThrLysLeuGlyLysAlaGlyTyrValThrAsnLysGlyArgGln
BM5   -------------------G--------------------------------------T--G--------         631
                         Ser                                                Arg

BM10  AAGGTTGTCCCCTAACTAACACAACAAATCAGAAAACTGAGTTACAAGCAATTTATCTAGCTTTGCAGGATTCA  3596
      LysValValProLeuThrAsnThrThrAsnGlnLysThrGluLeuGlnAlaIleTyrLeuAlaLeuGlnAspSer
BM5   ---A-----------C------------------G---------------C---------------G------  656
          Thr          His                                 Asn

BM10  GGATTAGAAGTAAACATAGTAACAGACTCACAATATGCATTAGGAATCATTCAAGCACAACCAGATAAAAGTGAA  3671
      GlyLeuGluValAsnIleValThrAspSerGlnTyrAlaLeuGlyIleIleGlnAlaGlnProAspLysSerGlu
BM5   -----T-----------------------------------------------------------------  681

BM10  TCAGAGTTAGTCAATCAAATAGAGCAGTTAATAAAGAAAGGTCTATCTGGCATGGTACCAGCACAC     3746
      SerGluLeuValAsnGlnIleGluGlnLeuIleLysLysLysGlyValTyrLeuAlaTrpValProAlaHis
BM5   ----------------------------------------------------------------        706
                                                               Lys I

BM10  AAAGGAATTGGAGGAAATGAACAAGTAGATAAATTAGTCAGTGCTGGAATCAGGAAATACTATTTTAGATGGA  3821
      LysGlyIleGlyGlyAsnGluGlnValAspLysLeuValSerAlaGlyIleArgLysTyrTyrPheLeuAspGly
BM5   --------------------------------------------------------------------    731
```

FIG. 3 (Continued)

```
BM10  ATAGATAAGGCCCAAGATGAACATGAGAAATATCACAGTAATTGGAGAGCCAATGGCTAGTGATTTTAACCTGCCA    3896
      IleAspLysAlaGlnAspGluMetGluLysTyrHisSerAsnTrpArgAlaMetAlaSerAspPheAsnLeuPro
BM5   ---------------------------------------A------------------------------------                                                                                756
                        Pvu II
BM10  CCTGTAGTAGCAAAAGAAATAGTAGCCAGCTGTGATAAATGTCAGTGCAAAAGGAGAAGCCATGCATGGACAAGTA    3971
      ProValAlaLysGluIleValAlaSerCysAspLysCysGlnLeuLysGlyGluAlaMetHisGlyGlnVal
BM5   ----------------------------------------------------------------------------                                                                                781
BM10  GACTGTAGTCCAGGAATATGGCAACTAGATTGTACACATTTAGAAGGAAAAGTTATCCTGGTAGCAGTTCATGTA    4046
      AspCysSerProGlyIleTrpGlnLeuAspCysThrHisLeuGluGlyLysValIleLeuValAlaValHisVal
BM5   ----------------------------------------------------------------------------                                                                                806
                                                                Aha III
BM10  GCCAGTGGATATATAGAAGCAGAAGTTATTCCAGCAGAAACAGGCAAACAGCATATTTCTTTAAAATTA         4121
      AlaSerGlyTyrIleGluAlaGluValIleProAlaGluThrGlyLysGlnHisIleSerLeuLysLeu
BM5   ----------------------------------------------------------------------------                                                                                831
BM10  GCAGGAAGATGGCCAGTAAAAACAATAACATACAGACAATGGCAGCAATTCACCAGTGCTACGGTTAAGGCCCGCC    4196
      AlaGlyArgTrpProValLysThrIleThrTyrArgGlnTrpGlnPheThrSerAlaThrValLysAlaAla
BM5   ----------------------------------------------------------------------------                                                                                856
                             Eco RI
BM10  TGTTGGTGGGCGGGAATCAAGCAGGAATTTGGAATTCCCTACAATCCCAAAGTCAAGCAGTAGTAGAATCTATG    4271
      CysTrpTrpAlaGlyIleLysGlnGluPheGlyIleProTyrAsnProGlnSerGlnValValGluSerMet
BM5   ----------------------------------------------------------------------------                                                                                881
BM10  AATAAAGAATTAAAGAAAATTATAGGACAGGTAAGAGATCAGGCTGAACATCTTAAGACAGCAGTACAAATGGCA    4346
      AsnLysGluLeuLysLysIleIleGlyGlnValArgAspGlnAlaGluHisLeuLysThrAlaValGlnMetAla
BM5   ----------------------------------------------------------------------------                                                                                906
```

FIG. 3 (Continued)

```
         Aha III
BM10 GTATTCATCCACAATTTTAAAAGAAGAAATAGAAAAAAGAAGGGGATTGGGGGTACAGTGCAGGGAAAGAATAGTAGACATAATA    4421
     ValPheIleHisAsnPheLysArgLysArgLysGlyIleGlyGlyIleGlyGlyTyrSerAlaGlyGluArgIleValAspIleIle    931
BM5  ------------------------------------------------------------------------------------

BM10 GCAACAGACATACAAACTAAAGAATTACAAAAACAAATTCAAATTTTCGGGTTTATTACAGGGAC                          4496
     AlaThrAspIleGlnThrLysGluLeuGlnLysGlnIleLeuThrLysIleGlnAsnPheArgValTyrTyrArgAsp           956
BM5  ------------------------------------------------------------------

BM10 AGCAGAAATCCACTTTGGAAGGACCAGCAAAGCTCCTCTGGAAAGGTGAAGGGCAGTAGTAGTAATACAAGATAAT              4571
     SerArgAsnProLeuTrpLysAspGlnProAlaLeuLysLeuLeuTrpLysGlyGlyAlaValValIleGlnAspAsn           981
BM5  ---------------------------------------------------------------------------
         SOR

BM10 AGTGACATAAAAGTAGTGCCAAGAGAAAAGCAAAGATCATTAGGAGAAAACAGATGGCAGGTGATGAT                      4646
     SerAspIleLysValValProArgArgLysAlaLysIleIleArgArgSerTyrGlyLysGlnMetAlaGlyAspAsp           1006
BM5  --------------------------------------------------------------------                     20
     CysGlnGluGluLysGlnArgSerLeuGlyIleMetGluAsnArgTrpGlnValMetIle
           POL

BM10 TGTGTGGCAAGTAGACAGGATGAGGATTAGAACATGGAAAAGTTAGTAAAACACCATATGTATGTTTCAGGGAA                4721
     CysValAlaSerArgGlnAspGluAsp                                                              1015
     ValTrpGlnValAspArgMetArgIleArgThrTrpLysSerLeuValLysHisMetTyrValSerGlyLys                 45
BM5  -------------------------------------------G----------------------
                                                Arg

BM10 AGCTAGGGGATGGTTTATAGACATCACTATGAAAGCCCTCATCCAAGAATAAGTTCAGAAGTACACATCCCACT                4796
     AlaArgGlyTrpPheTyrArgHisHisTyrGluArgHisProArgIleSerSerGluValHisIleProLeu                 70
BM5  -------------------------------------------------------------------

BM10 AGGGGGATGCTAGATTGGTAATAACAACATATTGGGTCTGCATACAGGAGAAAGAGACTGGCATTGGGTCAGGG                4871
     GlyAspAlaArgLeuValIleThrThrTyrTrpGlyLeuHisThrGlyLeuArgAspArgAspTrpHisLeuGlyGlnGly        95
BM5  ---------------------------------------------------------------------------
```

FIG. 3 (Continued)

```
BM10  AGTCTCCATAGAATGGAGGAAAAAGAGATATAGCACACAAGTAGACCCTGAACTAGCAGACCAACTAATTCATCT  4946
         ValSerIleGluTrpArgLysLysArgTyrSerThrGlnValAspProGluLeuAlaAspGlnLeuIleHisLeu
BM5   -------------------------G------------------------------------------------
                               Arg

BM10  GTATTACTTTGACTGTTTTCAGACTCTGCTATAAGAAGGCCTTATTAGGACACATAGTTAGCCCTAGGTGTGA  5021
         TyrTyrPheAspCysPheSerAspSerAlaIleArgLysAlaLeuLeuGlyHisIleValSerProArgCysGlu
BM5   -C----------T------------------------------------------------------------

BM10  ATATCAAGCAGGACATAACAAGGTAGGATCTCTACAATACTTGGCACTAGCAGCATTAATAACACCAAAAAGAT  5096
         TyrGlnAlaGlyHisAsnLysValGlySerLeuGlnTyrLeuAlaLeuAlaLeuIleThrProLysLysIle
BM5   ---A-----------------------------------------------------------G---------
                                                                        Val

BM10  AAAGCCACCTTTGCCTAGTGTTACGAAACTGACAGAGGATAGATGGAACAAGCCCCAGAAGACCAAGGGCCACAG  5171
         LysPr ProLeuProSerValThrLysLeuThrGluAspArgTrpAsnLysProGlnLysThrLysGlyHisArg
                SOR
BM5   -------------------------------------------------------------------------

BM10  AGGGAGCCACACAATGAATGGACACTAGAGCTTTAGAGGAGCTTAAGAATGAAGCTGTTAGACATTTCCTAGG  5246
         GlySerHisThrMetAsnGlyHis
BM5   ---A---------------------------------------------------------------------

BM10  ATTTGGCTCCATGGCTTAGGGCAACATATCTATGAAACTTATGGGATACTTGGGCAGGAGTGGAAGCCATAATA  5321
BM5   -------------------------------------------------------------------------
      EcRI
BM10  AGAATTCTGCAACAACTGCTGTTTATCCATTTTCAGAATTGGGTGTCGACATAGCAGAGAATAGGCGTTACTCGACA  5396
                                                  SalI
BM5   -----------------------------------------------------------------A----
```

FIG. 3 (Continued)

```
BM10  GAGGAGAGCAAGAAATGGAGCCAGTAGATCCTAGAGCCCTGGAAGCATCCAGGAAGTCAGCCTAAAACTG    5471
BM5   ------------------------------------------------------------------

BM10  CTTGTACCAATTGCTATTGTAAAAGTGTTGCTTTCATTGCCAAGTTTGTTTCATACAAAAGCCTTAGGCATCT  5546
BM5   -----------------C---------------------------------------------------
                                     (Sst I)
BM10  CCTATGGCAGGAAGAAGCGGACGAAGACCTCCTCAAGGCAGTCAGACTCATCAAGTTTCTCTATCAA       5621
BM5   -----------------------G---------------------------------------
BM8   ---G---A---G---A----------------------------------------------

BM10  AGCAGTAAGTAGTACATGTAATGCAACCTATACAAATAGCAATAGTAGCAT ITTAGTAGTAGCAATAATAATAGCAA  5696
BM8   ----------------------C------------T---C---A---T-GCC-----C-----------

BM10  TAGTTCTGTGGTCCATAGTAATCATAGTAATATAGGAAATATTAAGACAAAGAAAATAGACAGGTTAATTGATA  5771
BM8   -------------------------------------------------------------------
           ENV-LOR
BM10  GACTAATAGAAAGAGAACAGGAAGCAGTGGCAATGAGAGTGAAGGAGAAATATCAGCACTTGTGGAGATGGGGTGG  5846
BM8   -------------------------------------------------------------------
      LysGluGlnLysThrValAlaMetArgValLysGluLysTyrGlnHisLeuTrpArgTrpGlyTrp

BM10  AGATGGGGCACCATGCTCCTTGGGATGTTGATGATCTGTAGTGCTACAGAAAATTGTGGGTCACAGTCTATTAT   5921
BM8   ----------------------------------------------------------------
      ArgTrpGlyThrMetLeuLeuGlyMetLeuMetIleCysSerAlaThrGluThrValThrValTyrTyr-
                                                                      Phe
      Kpn I
BM10  GGGGTACCTGTGTGGAAGGAAGCAACCACCACTCTATTTTGTGCATCAGATGCTAAAGCATATGATACAGAGGTA   5996
BM8   -------------------------------------------------------------------
      GlyValProValTrpLysGluAlaThrThrThrLeuPheCysAlaSerAspAlaLysAlaTyrAspThrGluVal
```

```
                              *                                    Hind III
BH10  AATAAATCTCTGGAACAGATTTGGAATAACATGACCTGGATGGAGTGGGACAGAGAAATTAACAATTACACAAGC    7721
      AsnLysSerLeuGluGlnIleTrpAsnAsnMetThrTrpMetGluTrpAspArgGluIleAsnAsnTyrThrSer
BH8   ----------------------------------------------------------------------------

BH10  TTAATACACTCCTTAATTGAAGAATCGCAAAACCAGCAAGAATGAACAAGAATTATTGGAATTAGATAAA         7796
      LeuIleHisSerLeuIleGluGluSerGlnAsnGlnGlnGluLysAsnGluGlnGluLeuLeuGluLeuAspLys
BH8   ----------------------------------------------------------------------------

BH10  TGGGCAAGTTTGTGGAATTGGTTTAACATAACAAATTGGCTGTGGTATATAAAATTATTCATAATGATAGTAGGA    7871
      TrpAlaSerLeuTrpAsnTrpPheAsnIleThrAsnTrpLeuTrpTyrIleLysLeuPheIleMetIleValGly
BH8   -------A--------------------------------------------------------------------
                                                                   Ile

BH10  GGCTTGGTAGGTTTAAGAATAGTTTTTGCTGTACTTTCTGTAGTGAATAGAGTTAGACAGGGATATTCACCATTA    7946
      GlyLeuValGlyLeuArgIleValPheAlaValLeuSerValValAlaAsnArgValArgGlnGlyTyrSerProLeu
BH8   ----------------A----------------------------------------------------------
                    Asn

BH10  TCGTTTCAGACCCACCTCCCAATCCCGAGGGGACCCGACAGGCCCGAAGGAATAGAAGAAGAAGGTGGAGAGAGA    8021
      SerPheGlnThrHisLeuProIleProArgGlyProAspArgProGluGlyIleGluGluGluGlyGlyGluArg
BH8   ----------------------------------------------------------------------------

BH10  GACAGAGACAGATCCATTCGATTAGTGAACGGATCCTTAGCACTTATCTGGGACGATCTGCGGAGCCTGCCTC     8096
      AspArgAspArgSerIleArgLeuValAsnGlySerLeuAlaLeuIleTrpAspAspLeuArgSerLeuCysLeu
BH8   ----------------------------------------------------------------------------

BH10  TTCAGCTACCACCGCTTGAGAGACTTACTCTTGATTGTAACGAGGATTGTGGAACTTCTGGGACGCAGGGGTGG    8171
      PheSerTyrHisArgLeuArgAspLeuLeuLeuIleValThrArgIleValGluLeuLeuGlyArgArgGlyTrp
BH8   ----------------------------------------------------------------------------
```

```
BH10  CAGATATCCACTGACCTTTGGATGGTGCTACAAGCTAGTAGTTGAGCCAGAGAAGTTAGAGAAGAAGCCAACAA   8846
BH8   ------------------------------------------A-----------------------------T--

BH10  AGGAGAGAACACCAGCTTGTTACACCCCTGTGAGCCTGCATGGAATGACCCGGAGAGAGAAGTGTTAGAGTG     8921
BH8   ---------------------------------------------------T--------------------

BH10  GAGGTTTGACAGCCGCCTAGCATTTCATCACATGGCCCGAGAGCTGCATCCGGAGTACTTCAAGAACTGCTGACA  8996
BH8   ------------------------------------------------------------------------T--

BH10  TCGAGCTTGCTACAAGGGACTTTCCGCTGGGGACTTTCCAGGGAGGCGTGGCCTGGGCGGGACTGGGGAGTGGCG 9071
BH8   --------------------------------------------
                                       Pvu II      U3 ──R

BH10  AGCCCTCAGATCCTGCATATAAGCAGCTGCTTTTTGCCTGTACTGGGTCTCTCTGGTTAGACCAGATCTGAGCCT 9146
BH8   --------------------------------------------
      Sst I                                            Bgl II
      R
BH10  GGGAGCTC                                                                    9154
BH8   --------

Hind III
                                              Poly(A) Sig.    R
MXB2  TCTGGCTAGCTAGGGAACCCACTGCTTAAGCCTCAATAAAGCTTGCCTTGAGTGCTTCA                 9213
                                              ──U5
MXB2                                           AGTAGTGTGCCCGTCTGTTGTGTGACTCTGGTAACTAGAGATCCCTCAGA
                                                  U5
                                                  ──IR
MXB2  CCCTTTTAGTCAGTGTGGAAAATCTCTAGCA
```

CLONING AND EXPRESSION OF HTLV-III DNA

This application is a divisional application of U.S. application Ser. No. 06/693,866, filed Jan. 23, 1985, which is a continuation-in-part application of U.S. application Ser. No. 06/659,339, filed Oct. 10, 1984, abandoned, which is a continuation-in-part application of U.S. application Ser. No. 06/643,306, filed Aug. 22, 1984, now abandoned.

TECHNICAL FIELDS

This invention is in the fields of molecular biology and virology and in particular relates to human T cell leukemia virus—type III (HTLV-III).

BACKGROUND

The term human T cell leukemia-lymphoma virus (HTLV) refers to a unique family of T cell tropic retroviruses. These viruses play an important role in the pathogenesis of certain T cell neoplasms. There are presently three known types of HTLVs. One subgroup of the family, HTLV-type I (HTLV-I), is linked to the cause of adult T-cell leukemia-lymphoma (ATLL) that occurs in certain regions of Japan, the Caribbean and Africa. HTLV-type II (HTLV-II) has been isolated from a patient with a T-cell variant of hairy cell leukemia. M. Popovic et al., Detection, Isolation, and Continuous Production of Cytopathic Retroviruses (HTLV-III) from Patients with AIDS and Pre-AIDS. *Science*, 224:497–500 (1984).

HTLV-type III (HTLV-III) has been isolated from many patients with acquired immunodeficiency syndrome (AIDS). HTLV-III refers to prototype virus isolated from AIDS patients. Groups reported to be at greatest risk for AIDS include homosexual or bisexual males; intravenous drug users and Haitian immigrants to the United States. Hemophiliacs who receive blood products pooled from donors and recipients of multiple blood transfusions are also at risk. Clinical manifestations of AIDS include severe, unexplained immune deficiency which generally involves a depletion of helper T lymphocytes. These may be accompanied by malignancies and infections. The mortality rate for patients with AIDS is high. A less severe form of AIDS also exists, in which there may be lymphadenopathy and depressed helper T cell counts; there is not, however, the devastating illness characteristic of full-blown AIDS. There are many individuals, who are classified as having early AIDS (pre-AIDS), who exhibit these signs. It is not now possible to predict who among them will develop the more serious symptoms.

Much of the evidence implicates HTLV-III as the etiological agent of the infectious AIDS. First, there is consistent epidemiology; greater than 95% of the patients with AIDS have antibodies specific for HTLV-III. Second, there has been reproducible identification and isolation of virus in this disease; more than 100 variants of HTLV-III have been isolated from AIDS patients. Third, there has been transmission of the disease to normal healthy individuals who received blood transfusions from infected blood donors.

HTLV-III has been shown to share several properties with HTLV-I and HTLV-II but also to be morphologically, biologically and antigenically distinguishable. R. C. Gallo et al., Frequent Detection and Isolation of Cytopathic Retroviruses (HTLV-III) from Patients with AIDS and At Risk for AIDS. *Science*, 224:500–503. (1984). For example, HTLV-III has been shown to be antigenically related to HTLV-I and HTLV-II by demonstrating cross-reactivity with antibodies to HTLV-I and HTLV-II core proteins, p24 and p19, and envelope antigens and by nucleic acid cross-hybridization studies with cloned HTLV-I and HTLV-II DNAS. However, unlike HTLV-I and HTLV-II, it lacked the ability to infect and transform T cells from normal umbilical cord blood and bone marrow in vitro, and has the cytopathic effect on infected cells only.

Like the RNA genome of other retroviruses, the RNA genome of HTLV-III contains three genes which encode viral proteins: 1) the gag gene, which encodes the internal structural (nucleocapsid or core) proteins; 2) the pol gene, which encodes the RNA-directed DNA polymerase (reverse transcriptase); and 3) the env gene, which encodes the envelope glycoproteins of the virion. In addition, the HTLV-III genome contains a region designated Px, located between the env gene and the 3' LTR, which appears to be involved in functional killing of the virus.

At this time, AIDS is still difficult to diagnose before the onset of clinical manifestations. There is no method presently available for the prevention of the disease. Treatment of those with AIDS is generally not successful and victims succumb to the devastating effects HTLV-III has on the body.

SUMMARY OF THE INVENTION

This invention is based upon applicant's cloning of HTLV-III DNA in recombinant/vector host systems capable of expressing immunoreactive HTLV-III polypeptides. Based on the cloning of HTLV-III DNA in systems which express immunoreactive-polypeptides, applicant has developed methods useful in the diagnosis, treatment and prevention of AIDS. Applicant has developed methods of detecting HTLV-III and antibodies against HTLV-III in body fluids (e.g., blood, saliva, semen), and methods useful in immunotherapy (e.g., vaccination and passive immunization against AIDS). In addition, applicant has developed methods of making HTLV-III DNA probes and RNA probes useful in detecting HTLV-III in body fluids.

Polypeptides encoded by segments of the HTLV-III genome have been produced by these recombinant DNA methods. For example, polypeptides encoded by three regions of the HTLV-III genome (an env gene sequence, an env-lor gene sequence and a 1.1 Kb EcoRI restriction fragment from HTLV-III cDNA) have been produced. The polypeptides expressed have been isolated. These polypeptides are immunoreactive with sera of patients having AIDS and with antibodies to HTLV-III and thus are useful in screening blood and other body fluids for the presence of antibodies against HTLV-III. Applicant's invention therefor provides a method not only for diagnosing AIDS, but also for preventing the transmission of the disease to others through blood or blood components harboring HTLV-III. The latter is particularly valuable in screening donated blood before it is transfused or used to obtain blood components (e.g., Factor VIII for the treatment of hemophilia; Factor IX)

Polypeptides produced by the recombinant DNA methods are employed in the production of antibodies, including monoclonal antibodies, against the virus. Such antibodies form the basis for immunoassay and diagnostic techniques for directly detecting HTLV-III in body fluids such as blood, saliva, semen, etc. Neutralizing antibodies against the virus may be used to passively immunize against the disease.

Applicant's cloning of HTLV-III DNA in such recombinant vector host systems also provides the basis for determination of the nucleotide sequence of HTLV-III DNA. The DNA probes are homologous to DNA regions which are unique to the HTLV-III genome. DNA probes provide another method of detecting HTLV-III in blood, saliva or other body fluids. RNA probes which contain regions unique to the HTLV-III genome can also be formed and used for the detection of HTLV-III in body fluids.

BRIEF DESCRIPTION OF THE FIGURES

FIG. 1a shows sites at which the genome is cut by the restriction enzyme SstI and FIG. 1b shows the fragments of HTLV-III genome produced through the action of restriction enzymes Kpn, EcoRI and HindIII.

FIG. 2a shows the location of restriction enzyme sites in the genome and FIG. 2b shows the location in the HTLV-III genome of DNA inserts in open reading frame clones. The (+) and (−) indicate reactivity and lack of reactivity, respectively, of the fusion protein expressed by cells transformed by the ORF vectors with sera of AIDS patients.

FIG. 3 shows the nucleotide sequence for HTLV-III DNA SEQ ID NO:4 and the predicted amino acid sequence of the four longest open reading frames SEQ ID NOS:8–11. Restriction enzyme sites are indicated above the nucleotide sequence.

BEST MODE OF CARRYING OUT THE INVENTION

Figure 1:
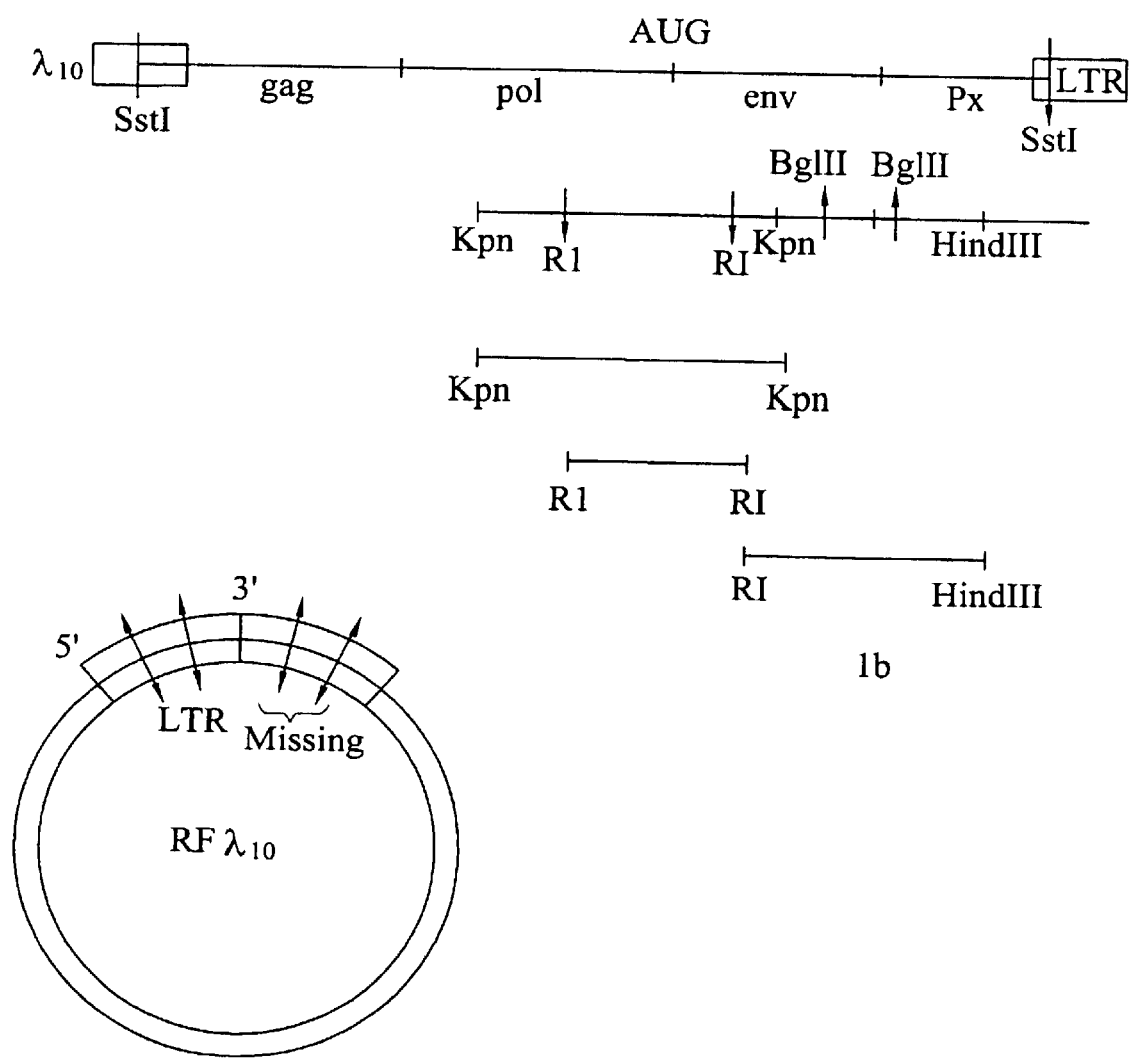
FIG. 1 is a representation of HTLV-III DNA.

Despite the similarity between HTLV-III and the other members of the HTLV-bovine leukemia virus (BLV) family of viruses, the biology and pathology of HTLV-III differs substantially. For example, relatively little homology has been found in the HTLV-III genome when compared with that of the HTLV-I or -II genome. Infection with HTLV-III often results in profound immunosuppression (AIDS), consequent to the depletion of the OKT4(+) cell population. This effect is mirrored by a pronounced cytopathic, rather than transforming, effect of HTLV-III infection upon the OKT4(+) cells in lymphocyte cultures in vitro. In contrast, infection with HTLV-I results in a low incidence of T-cell leukemia lymphoma (an OKT4(+) cell malignancy). There is evidence for some degree of immunodeficiency in HTLV-I patients as well. Infection of primary lymphocytes in culture by HTLV-I and -II results in vitro transformation of predominantly OKT4(+) cells. A cytopathic effect of HTLV-I infection upon lymphocytes is apparent, but the effect is not as pronounced as that observed for HTLV-III.

HTLV-III also differs from HTLV-I and -II in the extent of infectious virion production in vivo and in vitro. High titers of cell free, infectious virions can be obtained from AIDS patient semen and saliva and from the supernatant of cultures infected with HTLV-III. Very few, if any, cell free infectious virions can be recovered from adult T-cell leukemia lymphoma (ATLL) patients or from cultures infected with HTLV-I or -II.

Envelope glycoprotein is the major antigen recognized by the antiserum of AIDS patients. In this respect, HTLV resembles other retroviruses, for which the envelope glycoprotein is typically the most antigenic viral polypeptide. In addition, the neutralizing antibodies are generally directed toward the envelope glycoprotein of the retrovirus. Serum samples from 88 percent to 100 percent of those with AIDS have been shown to have antibodies reactive with antigens of HTLV-III; the major immune reactivity was directed against p41, the presumed envelope antigen of HTLV-III. Antibodies to core proteins have also been demonstrated in serum of AIDS patients, but do not appear to be as effective an indicator of infection as is the presence of antibodies to envelope antigen.

The p41 antigen of HTLV-III has been difficult to characterize because the viral envelope is partially destroyed during the process of virus inactivation and purification. This invention responds to the great need to characterize this antigenic component of the HTLV-III virus and to determine the existence and identity of other viral antigenic components in several ways. It provides products, such as HTLV-III polypeptides, antibodies to the polypeptides and RNA and DNA probes, as well as methods for their production. These serve as the basis for screening, diagnostic and therapeutic products and methods.

This invention relates to HTLV-III polypeptides which are produced by translation of recombinant DNA sequences encoding HTLV-III proteins. Polypeptides which are produced in this way and which are immunoreactive with serum from AIDS patients or antibodies to HTLV-III are referred to as recombinant DNA-produced immunoreactive HTLV-III polypeptides. They include, but are not limited to, antigenic HTLV-III core and envelope polypeptides which are produced by translation of the recombinant DNA sequences specific to the gag and the env DNA sequences encoding HTLV-III core proteins and envelope glycoproteins, respectively. They also include the polypeptides which are produced by translation of the recombinant DNA sequences included in a 1.1 Kb EcoRI restriction fragment of HTLV-III cDNA and recombinant DNA sequences specific to the sor gene and the Px genes of HTLV-III. The sor DNA sequence is common to replication competent HTLV-III viruses. The Px genes contain a coding sequence with one large open reading frame (lor), located between the env gene and the 3' end of the HTLV-III genome. Both the env DNA sequences and the lor DNA sequences are located within the same open reading frame of the HTLV-III genome and this gene region is accordingly designated env-lor.

The polypeptides encoded by these regions of the HTLV III can be used in immunochemical assays for detecting antibodies against HTLV-III and HTLV-III infection. These methods can assist in diagnosing AIDS. In addition, they can also be employed to screen blood before it is used for transfusions or for the production of blood components (e.g., Factor VIII for the treatment of hemophilia). Availability of screening techniques will reduce the risk of AIDS transmission.

Detection of antibodies reactive with the polypeptides can be carried out by a number of established methods. For example, an immunoreactive HTLV III polypeptide can be affixed to a solid phase (such as polystyrene bead or other solid support). The solid phase is then incubated with blood sample to be tested for antibody against HTLV-III. After an appropriate incubation period the solid phase and blood sample are separated. Antibody bound to the solid phase can be detected with labeled polypeptide or with a labeled antibody against human immunoglobulin.

HTLV-III polypeptides can be used in a vaccine useful for prevention of AIDS. For vaccination against the virus, immunogenic polypeptides which elicit neutralizing antibody would be employed. The leading candidates for use in vaccines are the viral envelop polypeptides.

The polypeptides can also be used to produce antibodies, including monoclonal antibodies, against the HTLV-III polypeptides. These antibodies can be used in immunochemical assays for direct detection of the virus in body fluids (such as blood, saliva and semen). Assays employing monoclonal antibody against specific HTLV III antigenic determinants will reduce false-positive results thereby improving accuracy of assays for the virus. Antibodies against the virus may also be useful in immunotherapy. For example, antibodies may be used to passively immunize against the virus.

The methods of producing the polypeptides are also a subject of this invention, as are diagnostic methods based on these polypeptides.

This invention also provides methods for the isolation of genes of HTLV-III which encode immunoreactive polypeptides; identification of the nucleotide sequence of these genes; introduction of DNA sequences specific to these viral DNA sequences into appropriate vectors to produce viral RNA and the formation of DNA probes. These probes are comprised of sequences specific to HTLV-III DNA and are useful, for example, for detecting complementary HTLV-III DNA sequences in body fluids (e.g., blood).

HTLV-III Polypeptides

Genetic engineering methods are used to isolate segments of HTLV-III DNA which encode immunoreactive HTLV-III polypeptides. Among these are polypeptides which are immunoreactive with serum from AIDS patients or antibodies to HTLV-III. These polypeptides include the core protein, a 15 Kd peptide encoded by a 1.1 Kb EcoRI HTLV-III restriction fragment of HTLV-III DNA and the envelope glycoprotein. These methods are also used to sequence the fragments which encode the polypeptides. The proviral genes integrated into host cell DNA are molecularly cloned and the nucleotide sequences of the cloned provirus is determined.

An *E. coli* expression library of HTLV-III DNA is constructed. The HTLV-III genome is cloned and cuts are then made in the cloned HTLV-III genome with restriction enzymes to produce DNA fragments. (FIGS. 1 and 2) HTLV-III DNA fragments of approximately 200–500 bp are isolated from an agarose gel, end repaired with $T_4$ polymerase and ligated to linker DNA. The linker ligated DNA is then treated with a restriction enzyme, purified from agarose gel and cloned in an expression vector. Examples of the expression vectors used are: OmpA, pIN (A,B and C), lambda pL, T7, lac, Trp, ORF and lambda gt11. In addition, mammalian cell vectors such as pSV2apt, pSV2neo, pSVdhfr and VPV vectors, and yeast vectors, such as GALI and GAL10, may be used.

The bacterial vectors contain the lac coding sequences, into which HTLV-III DNA can be inserted for the generation of B-galactosidase fusion protein. The recombinant vectors are then introduced into bacteria (e.g., *E.coli*); those cells which take up a vector containing HTLV-III DNA are said to be transformed. The cells are then screened to identify cells which have been transformed and are expressing the fusion protein. For example, the bacteria are plated on MacConkey agar plates in order to verify the phenotype of clone. If functional B-galactosidase is being produced, the colony will appear red.

Bacterial colonies are also screened with RTLV-III DNA probes to identify clones containing the DNA regions of interest (e.g., HTLV-III gag, pol and env DNA sequences). Clones which are positive when screened with the DNA probe and positive on the MacConkey agar plates are isolated.

This identification of cells harboring the HTLV-III DNA sequences makes it possible to produce HTLV-III polypeptides which are immunoreactive with HTLV-III specific antibody. The cells from the selected colonies are grown in culture under conditions allowing the expression of the hybrid protein. Cell protein is then obtained by means known in the art. For example, the culture can be centrifuged and the resulting cell pellet broken. Polypeptides secreted by the host cell can be obtained (without disruption of the cells) from the cell culture supernatant.

The total cellular protein is analysed by being run on an SDS polyacrylamide gel electrophoresis. The fusion proteins are identified at a position on the gel which contains no other protein. Western blot analyses are also carried out on the clones which screened positive. Such analyses are performed with serum from AIDS patients, with the result that it is possible to identify those clones expressing HTLV-III B-galactosidase fusion proteins (antigens) that cross-react with the HTLV-III specific antibody.

$Lambda_{10}$ clones harboring HTLV-III DNA are cloned from the replicated form of the virus. As the retrovirus is replicating, double stranded DNA is being produced. The cloned HTLV-III DNA is digested with the restriction enzyme SstI. (FIG. 1*a*) Because there are two SstI recognition sites within the LTR of HTLV-III DNA, one LTR region is not present in the cloned DNA sequence removed from the $lambda_{10}$ vector. As a result, a small (approximately 200 bp) fragment of the HTLV-III DNA is missing.

The resulting DNA is linearized and fragments are produced by digesting the linearized genomic DNA spanning the env gene region with restriction enzymes. For example, fragments are produced using KpnI or EcoRI plus HindIII, as shown in FIG. 1*b*. The resulting 2.3 kb KpnI-KpnI fragments; 1.0 kbEcoRI-EcoRI fragments and 2.4 kb EcoRI-HindIII fragments are isolated by gel electrophoresis and electroelution. These fragments are randomly sheared to produce smaller fragments. The fragments thus produced are separated on an agarose gel and DNA fragments between about 200–500 bp are eluted.

The eluted 200–500 bp DNA fragments are end filled through the use of *E. coli* $T_4$ polymerase and blunt end ligated into an open reading frame expression (ORF) vector, such as pMR100. This ligation may occur at the SmaI site of the pMR100 vector, which contains two promoter regions, hybrid coding sequences of lambdaCI gene and lacI-LacZ gene fusion sequence. In the vector, these are out of frame sequences; as a result, the vector is nonproductive. The HTLV-III DNA is inserted into the vector; the correct DNA fragments will correct the reading frame, with the result that CI-HTLV-III-B-galactosidase fusion proteins are produced. The expression of the hybrid is under the control of the lac promoter. Based on the sequence of pMR100, it appears that if a DNA fragment insert cloned into the SmaI site is to generate a proper open reading frame between the lambdaCI gene fragment and the lac-Z fragment, the inserted DNA must not contain any stop codons in the reading frame set by the frame of the lambdaCI gene.

The recombinant pMR100 vectors are then introduced into *E. coli*. The bacteria are plated on MacConkey agar plates to verify the phenotype of the clone. If functional B-galactosidase is being produced, the colony will appear red. The colonies are also screened with HTLV-III DNA probes, for the purpose of identifying those clones containing the insert. Clones which are positive when screened with the DNA probe and positive on the MacConkey agar plates are isolated.

The cells from the selected colonies are grown in culture. The culture is spun down and the cell pellet broken. Total cellular protein is analysed by being run on an SDS polyacrylamide gel. The fusion proteins are identified at a position on the gel which contains no other protein.

Western blot analyses are also carried out on the clones which screened positive. Sera from AIDS patients are used, thus making it possible to identify those clones which express the HTLV-III-B-galactosidase fusion proteins that cross-react with the HTLV-III specific antibody. 1000 clones were screened by this method; 6 were positive.

Because of the nature of the pMR100 cloning vehicle, a productive DNA insert should also be expressed as a part of a larger fusion polypeptide. HTLV-III env gene containing recombinant clones was identified by colony hybridization. The production of larger fusion polypeptides bearing functional B-galactosidase activity was verified by phenotype identification on MacConkey agar plates; by B-galactosidase enzymatic assays and by analysis on 75% SDS-polyacrylamide gels. Immunoreactivity of the larger protein with antibody to HTLV-III was assessed by western blot analysis using serum from AIDS patients. These large fusion proteins also reacted with anti-B-galactosidase and anti-CI antiserum. This finding is consistent with the hypothesis that they are proteins of CI-HTLV-III-lacIZ.

The open reading frame insert fragment of HTLV-III is further analyzed by DNA sequencing analysis. Because one of the two BamHI sites flanking the SmaI cloning site in pMR100 is destroyed in the cloning step, positive clones are digested with restriction enzymes HindIII and ClaI to liberate the inserted HTLV-III DNA fragment. The HTLV-III ORF inserts are isolated from the fusion recombinant and cloned into M13 sequencing cloning vector mp18 and mp19 digested with HindIll and AccI. DNA sequences of the positive ORF clones are then determined.

Fragments of HTLV-III DNA of approximately 200–500 bps are isolated from agarose gel, end repaired with $T_4$ polymerase and ligated to EcoRI linker. The EcoRI linker ligated DNA is then treated with EcoRI, purified from 1% agarose gel, and cloned in an expression vector, lambda gt11. This vector contains lac Z gene coding sequences into which the foreign DNA can be inserted for the generation of B-galactosidase fusion protein. The expression of the hybrid gene is under the control of lac repressor. The lac repressor gene, lac I, is carried on a separate plasmid pMC9 in the host cell, *E. coli* Y1090. AIDS patient serum was used to probe the lambda gt11 library of HTLV-III genome DNA containing $1.5 \times 10^4$ recombinant phage. In a screen of 5000 recombinants, 100 independent clones that produced strong signals were isolated. The positive recombinant DNA clones were further characterized for their specific gene expression. Rabbit hyperimmune serum against P24 was also used to identify the gag gene specific clones. Nick-translated DNA probes of specific HTLV-III gene, specifically the gag gene, env gene and Px gene were used to group the positive immunoreactive clones into specific gene region.

Recombinant clones that produced strong signals with AIDS serum and contain insert DNA spanning the HTLV-III gag, pol, sor and env-lor gene regions were examined in detail by mapping their insert with restriction enzymes and DNA sequencing analysis.

Determination of the Nucleotide Sequence of HTLV-III DNA

Genetic engineering methods are used to determine the nucleotide sequence of HTLV-III DNA. One technique that can be used to determine the sequence is a shotgun/random sequencing method. HTLV-III DNA is sheared randomly into fragments of about 300–500 bp in size. The fragments are cloned, for example, using m13, and the colonies screened to identify those having an HTLV-III DNA fragment insert. The nucleotide sequence is then generated, with multiple analysis producing overlaps in the sequence. Both strands of the HTLV-III DNA are sequenced to determine orientation. Restriction mapping is used to check the sequencing data generated.

Figure 3:
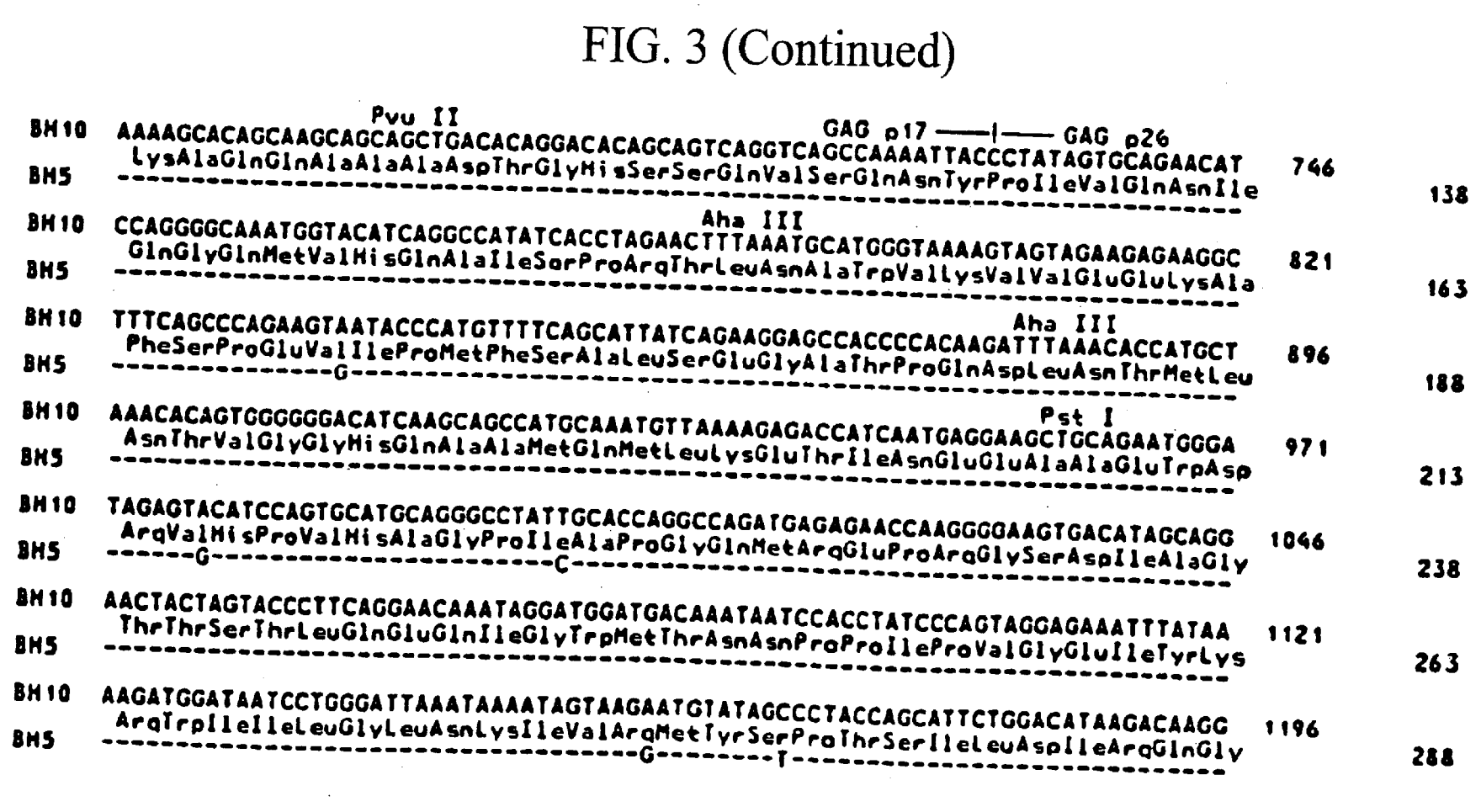
Figure 3:
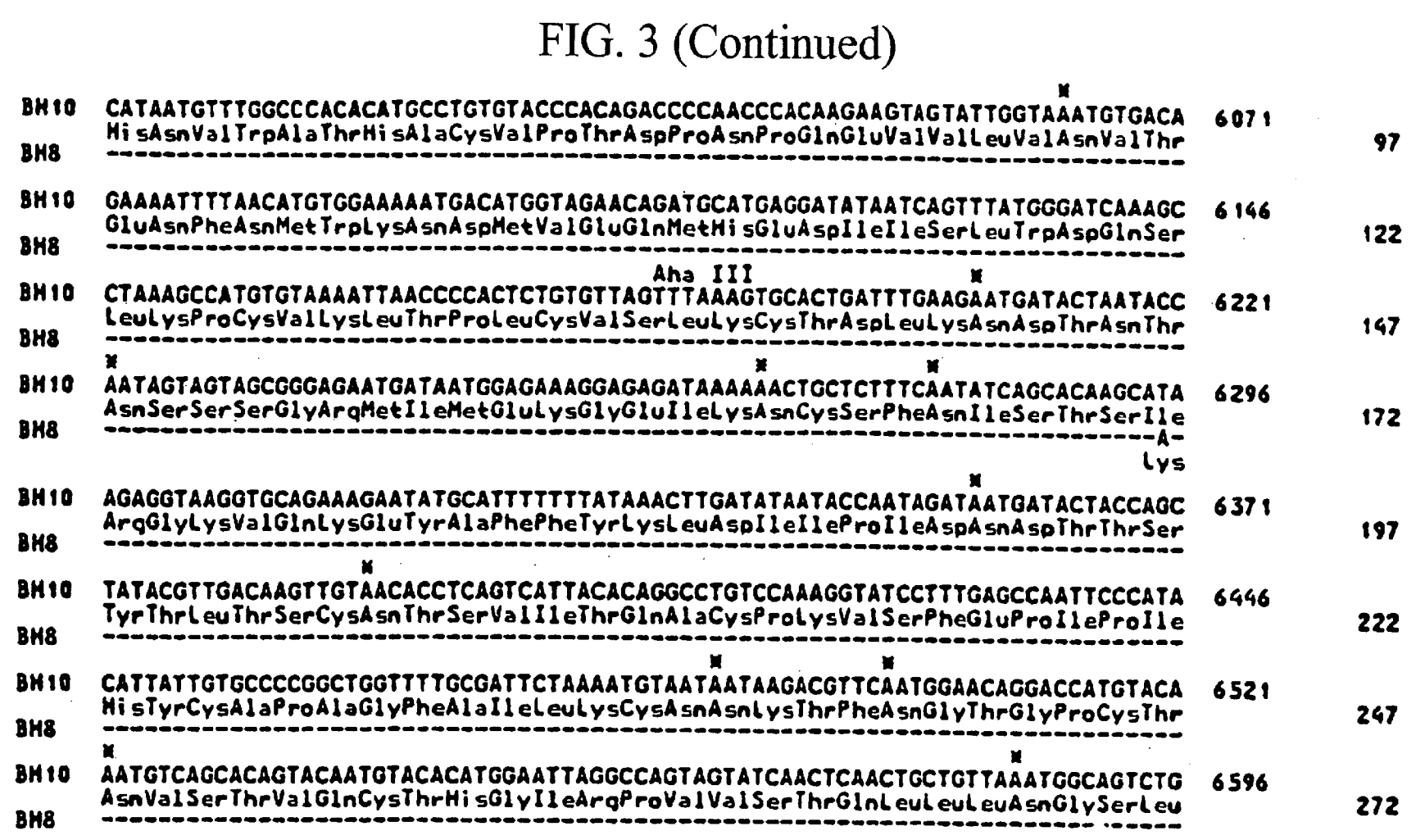
Figure 3:
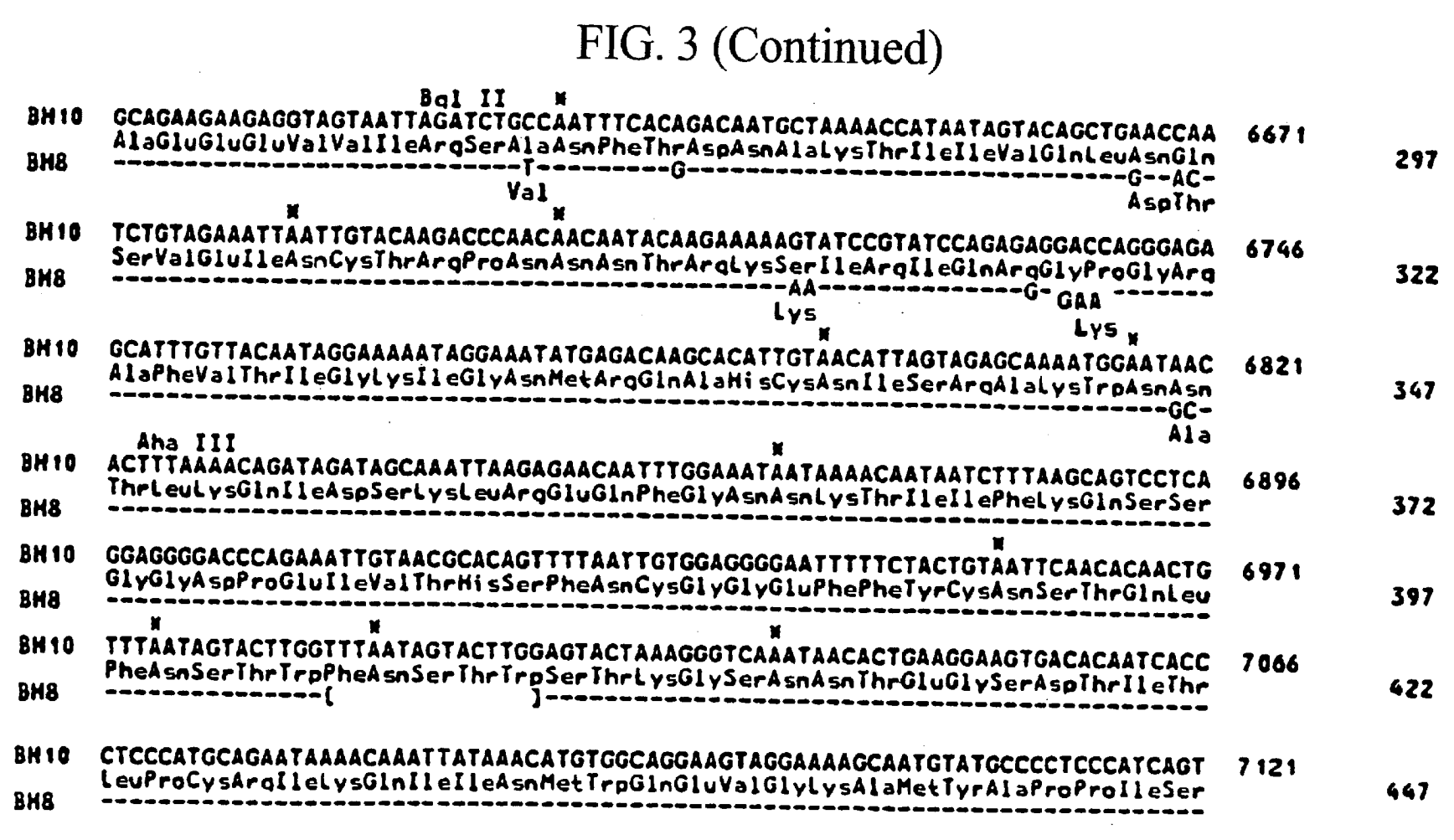
Figure 3:
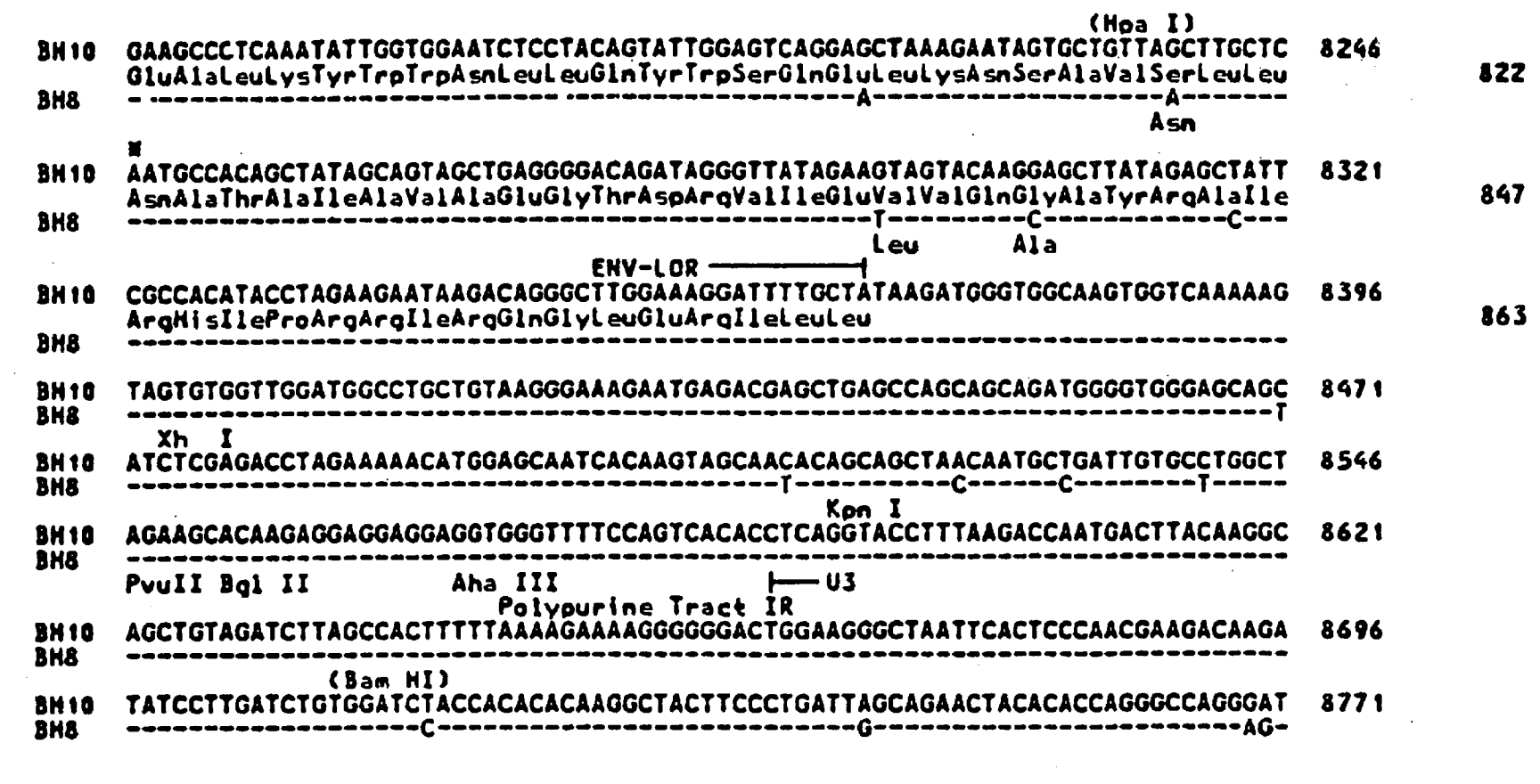

The nucleotide sequence of one cloned HTLV-III genome (BH10) is shown in FIG. 3, and SEQ ID NO:4 in which the position of sequences encoding gag protein p17 and the N-terminus of gag p24 and the C-terminus of gag p15 (which overlaps with the N-terminus of the pol protein) are indicated. The open reading frames (ORF) for pol, sor and env-lor are also indicated. The sequence of the remaining 182 base pairs of the HTLV-III DNA not present in clone BH10 (including a portion of R, U5, the tRNA primer binding site and a portion of the leader sequence) was derived from clone HXB2 (SEQ ID NO:3). The sequences of two additional clones (BHB and BH5 (SEQ ID NO:6)) are also shown. Restriction enzyme sites are listed above the nucleotide sequence; sites present in clone BHB but not in clone BH10 are in parentheses. Deletions are noted ([ ]) at nucleotides 251, 254, 5671 and 6987–7001. The nucleotide positions (to the right of each line) start with the transcriptional initiation site. The amino acid residues are numbered (to the right of each line) for the four largest open reading frames starting after the preceding termination codon in each case except gag which is enumerated from the first methionine codon. A proposed peptide cleavage site (V) and possible asparagine-linked glycosylation sites are shown (*) for the env-lor open reading frame. The sequences in the LTR derived from clones BH8 and BH10 (SEQ ID NO:6) listed in the beginning of the figure are derived from the 3'-portion of each clone and are assumed to be identical to those present in the 5'-LTR of the integrated copies of these viral genomes.

Recombinant phage clones harboring HTLV-III DNA, designated λBH-10, λBH-5 and λBH-8, were deposited with the American Type Culture Collection, 12301 Parklawn Drive, Rockville, Md., 20852 on Jul. 30, 1984 under ATCC accession numbers 40125, 40126, and 40127, respectively.

Clone HXB2 was derived from a recombinant phage library of XbaI digested DNA from HTLV-III infected H9 cells cloned in lambdaJ1, H9 cells are human leukemic cells infected by a pool of HTLV-III from blood of AIDS patients, F. Wong-Staal, *Nature,* 312, November 1984. Cloning vector clones BH10, BH8, and BH5 (SEQ ID NO:5) were derived from a library of SstI digested DNA from the Hirt supernatant fraction of HTLV-III infected H9 cells cloned in lambdagtWes.lambdaB. Both libraries were screened with cDNA probe synthesized from virion RNA using oligo-dT as a primer. Clones BH8, BH5, and a portion of HXB2 were sequenced as described by Maxam and Gilbert. (1980) Maxam, A. M. and Gilbert, Co. *Methods in Enzymology.* 65: 499–560. Clone BH10 was sequenced by the method of Sanger modified by the use of oligonucleotides complementary to the M13 insert sequence as primers and using Klenow fragment of DNA polymerase I or reverse transcriptase as the polymerase.

Formation of RNA, RNA Probes and DNA Probes Specific to HTLV-III

DNA sequences which are an entire gene or segment of a gene from HTLV-III are inserted into a vector, such as a T7 vector. In this embodiment, the vector has the Tceu promoter from the T cell gene 10 promoter and DNA sequences encoding eleven amino acids from the T cell gene 10 protein.

The vectors are then used to transform cells, such as *E. coli*. The T7 vector makes use of the T7 polymerase, which catalyzes RNA formation and recognizes only T7 promoter, which is the site where RNA polymerase binds for the initiation of transcription. The T7 polymerase does not recognize *E. coli* promotus. As a result, if HTLV-III DNA sequences are inserted after the promoter and polymerase genes of the T7 vector, which recognizes them to the exclusion of other signals, and a terminator is placed immediately after the HTLV-III DNA sequences, the T7 vector will direct manufacture RNA complementary to the HTLV-III DNA insert.

Determination of the nucleotide sequence of HTLV-III DNA also provides the basis for the formation of DNA probes. Both RNA probes and DNA HTLV-III probes must have a distinctive region of the HTLV-III genome in order to be useful in detecting HTLV-III in body fluids. There is relatively little homology between the HTLV-III genome and the HTLV-I and -II genomes and probes contain regions which are unique to HTLV-III (i.e., not shared with HTLV-I or -II). For example, nucleotide sequences in the env gene region of HTLV-III can be used.

Either viral RNA or DNA can be used for detecting HTLV-III in, for example, saliva, which is known to have a very high concentration of the virus. This can be done, for example, by means of a dot blot, in which the saliva sample is denatured, blotted onto paper and then screened using either type of probe. If saliva is used s the test fluid, detection of HTLV-III is considerably faster and easier than is the case if blood is tested.

Production of Monoclonal Antibodies Reactive with HTLV-III Polypeptides

Monoclonal antibodies reactive with HTLV-III polypeptides are produced by antibody-producing cell lines. The antibody-producing cell lines may be hybrid cell lines commonly known as hybridomas. The hybrid cells are formed by fusion of cells which produce antibody to HTLV-III polypeptide and an immortalizing cell, that is, a cell which imparts long term tissue culture stability on the hybrid cell. In the formation of the hybrid cell lines, the first fusion partner—the antibody-producing cell—can be a spleen cell of an animal immunized against HTLV-III polypeptide. Alternatively, the antibody-producing cell can be isolated B lymphocyte which produces antibody against an HTLV-III antigen. The lymphocyte can be obtained from the spleen, peripheral blood, lymph nodes or other tissue. The second fusion partner—the immortal cell—can be a lymphoblastoid cell or a plasmacytoma cell such as a myeloma cell, itself an antibody-producing cell but also malignant.

Murine hybridomas which produce monoclonal antibodies against HTLV-III polypeptide are formed by the fusion of mouse myeloma cells and spleen cells from mice immunized against the polypeptide. To immunize the mice, a variety of different immunization protocols may be followed. For instance mice may receive primary and boosting immunizations of the purified polypeptide. The fusions are accomplished by standard procedures. Kohler and Milstein, (1975) *Nature (London)* 256, 495–497; Kennet, R., (1980) in *Monoclonal Antibodies* (Kennet et al., Eds. pp. 365–367, Plenum Press, NY).

The hybridomas are then screened for production of antibody reactive with the polypeptide. This can be performed by screening procedures known in the art.

Another way of forming the antibody-producing cell line is by transformation of antibody-producing cells. For example, a B lymphocyte obtained from an animal immunized against HTLV-III polypeptide may be infected and transformed with a virus such as the Epstein-Barr virus in the case of human B lymphocytes to give an immortal antibody-producing cell. See, e.g., Kozbor and Rodor (1983) *Immunology Today* 4(3), 72–79. Alternatively, the B lymphocyte may be transformed by a transforming gene or transforming gene product.

The monoclonal antibodies against HTLV-III polypeptide can be produced in large quantities by injecting antibody-producing hybridomas into the peritoneal cavity of mice and, after an appropriate time, harvesting the ascites fluid which contains very high titer of homogenous antibody and isolating the monoclonal antibodies therefrom. Xenogeneic hybridomas should be injected into irradiated or athymic nude mice. Alternatively, the antibodies may be produced by culturing cells which produce HTLV-III polypeptide in vitro and isolating secreted monoclonal antibodies from the cell culture medium. The antibodies produced according to these methods can be used in diagnostic assays (e.g., detecting HTLV-III in body fluids) and in passive immunotherapy. The antibodies reactive with HTLV-III polypeptides provide the basis for diagnostic tests for the detection of AIDS or the presence of HTLV-III in biological fluids (e.g., blood, semen, saliva) and for passive immunotherapy. For example, it is possible to produce anti p 41, to attach it to a solid phase using conventional techniques and to contact the body fluid to be tested with the immobilized antibody. In this way, HTLV-III (antigen) can be detected in the body fluid; this method results in far fewer false positive test results than do tests in which antibody against HTLV-VIII is detected.

This invention will now be further illustrated by the following examples.

EXAMPLE 1

Preparation of Sonicated DNA Fragments

10 μg of gel purified HTLV-III restriction fragments were sonicated to fragment size on average of 500 bps. After sonication, the DNA was passed through a DEAE-cellulose column in 0.1×TBE in order to reduce the volume. The DEAE-bound DNA was washed with 5 ml of 0.2 M NaCl-TE (2 M NaCl, 10 mm Tris HCl pH 7.5, 1 mM EDTA) and then eluted with 1 M NaCl-TE, and ethanol precipitated. The size range of the sonicated DNA was then determined on 1.2% agarose gel. DNA fragments of desired length (200–500 bps) was eluted from the gel. T4 DNA polymerase was used to fill in and/or trim the single strand DNA termini generated by the sonication procedure. DNA fragments were incubated with T4 polymerase in the absence of added nucleotides for five minutes at 37° C. to remove nucleotides from the 3' end and then all 4 nucleotide precursors were added to a final concentration of 100 uM and the reaction mixture was incubated another 30 minutes to repair the 5'-end single stranded overhang. The reaction was stopped by heat inactivation of the enzyme at 68° C. for 10 minutes. DNA was phenol extracted once, ethanol precipitated and resuspended in TE.

EXAMPLE 2

Cloning of Random Sheared DNA Fragments

The sonicated blunt end repaired HTLV-III DNA fragments were ligated into the SmaI site of the ORF expression vector pMR100 and transformed into host cell LG90 using standard transformation procedures. B-galactosidase positive phenotype of the transformant were identified by plating the transformed cell on ampicillin (25 μg/ml) containing McConkey agar plates and scoring the phenotype after 20 hours at 37° C.

EXAMPLE 3

Hybrid Protein Analysis

Ten milliliter samples of cells from an overnight saturated culture grown in L broth containing ampicillin (25 μg/ml) were centrifuged, the cell pellet was resuspended in 500 μl of 1.2 fold concentrated Laemmli sample buffer. The cells were resuspended by vortexing and boiling for 3 minutes at 100° C. The lysate was then repeated by being forced through a 22 gauge needle to reduce the lysate viscosity. Approximately 10 μl of the protein samples were electrophoresed in 7.5% SDS-PAGE (SDS-polyacrylamide) gels.

Electrophoretic transfer of proteins from SDS-PAGE gels to nitrocellulose paper was carried out according to Towbin et. al. After the transfer, the filter was incubated at 37° C. for two hours in a solution of 5% (w/v) nonfat milk in PBS containing 0.1% antifoam A and 0.0001% merthiolate to saturate all available protein binding sites. Reactions with AIDS antisera were carried out in the same milk buffer containing 1% AIDS patient antisera that had been preabsorbed with E. coli lysate. Reactions were performed in a sealed plastic bag at 4° C. for 18–24 hours on a rotatory shaker. Following this incubation, the filter was washed three times for 20 minutes each at room temperature in a solution containing 0.5% deoxycholic, 0.1 M NaCl, 0.5% triton X-100, 10 mm phosphate buffer pH 7.5 and 0.1 mM PMSF.

To visualize antigen-antibody interactions, the nitrocellulose was then incubated with the second goat antihuman antibody that had been iodinated with $^{125}$I. The reaction with the iodinated antibody was carried out at room temperature for 30 minutes in the same milk buffer as was used for the first antibody. The nitrocellulose was then washed as previously described and exposed at –70° C. using Kodak XAR5 film with an intensifying screen.

EXAMPLE 4

Screening of the HTLV-III ORF Library by Colony Hybridization

E. coli LG90 transformants were screened with HTLV-III DNA probes containing the DNA regions of interest (e.g. HTLV-III gag, env or Px gene specific sequences). Colonies were grown on nitrocellulose filters and screened according to the procedure of Grunstein and Hogness by using a nick-translated HTLV-III DNA as hybridization probe.

The DNA fragment was in general excised by restriction endonuclease digestion, gel purified, and $^{32}$P-labeled to a specific activity of $0.5 \times 10^8$ cpm/μg by nick-translation (Rigby, P. W. J. et al., J. Mol. Biol. 113, 237 (1977). Duplicate nitrocellulose filters with DNA fixed to them were prehybridized with 6×SSC (0.9 M NaCl/0.09 M sodium citrate, pH 7.0), 5×Denhardt's solution (Denhardt's solution: 0.02% each of polyvinylpyrrolidone, Ficoll and bovine serum albumin) 10 μg of denatured sonicated E. coli DNA per ml at 55° C. for 3–5 hours. The filters were then placed in a fresh sample of the same solution to which the denatured hybridization probe had been added. Hybridization was permitted to take place at 68° C. for 16 hours. The filters were washed repeatedly in 0.3×SSC at 55° C., and then exposed to x-ray film.

EXAMPLE 5

Recombinant DNA Produced Peptide of HTLV-III which is Immunoreactive with SERA from Patients with AIDS An expression vector, pIN-III-ompA (ompA) was used. ompA has the lipoprotein (the most abundant protein in E.coli) gene promoter (1pp) and the lacUV5 promoter-operator (FIG. 1). ompA vectors also contain the DNA segment encoding the lac repressor, which allows the expression of the inserted DNA to be regulated by lac operon inducers such as IPTG. The ompA cloning vehicles contain three unique restriction enzyme sites EcoRI, HindIII, Bam HI in all three reading frames and permit the insertion of DNA into any of these restriction sites.

Various restriction fragments were excised from the recombinant clone, lambdaBH10, which contains a 9 Kb long HTLV-III DNA insert in the SstI site of the vector lambdagtWES lambdaB. These restriction fragments were them inserted into the ompA vectors at all three reading frames and used to transform E.coli JA221 cells. Transformants were first screened for HTLV-III DNA by in situ colony hybridization using nick-translated HTLV-III DNA probes. The positive clones were then screened for expression of HTLV-III antigenic peptides using HTLV-III specific antibodies. For this, lysates of E.coli cell containing HTLV-III DNA recombinant plasmids were electrophoresed on 12.5% SDS-polyacrylamide gel and electroblotted onto nitrocellulose filters. The filters were then incubated first with well-characterized sera from AIDS patients and next with $^{125}$I-labelled goat anti-human IgG antibodies. The washed filters were autoradiographed to identify peptides reactive with anti-HTLV-III antibodies.

Figure 4:
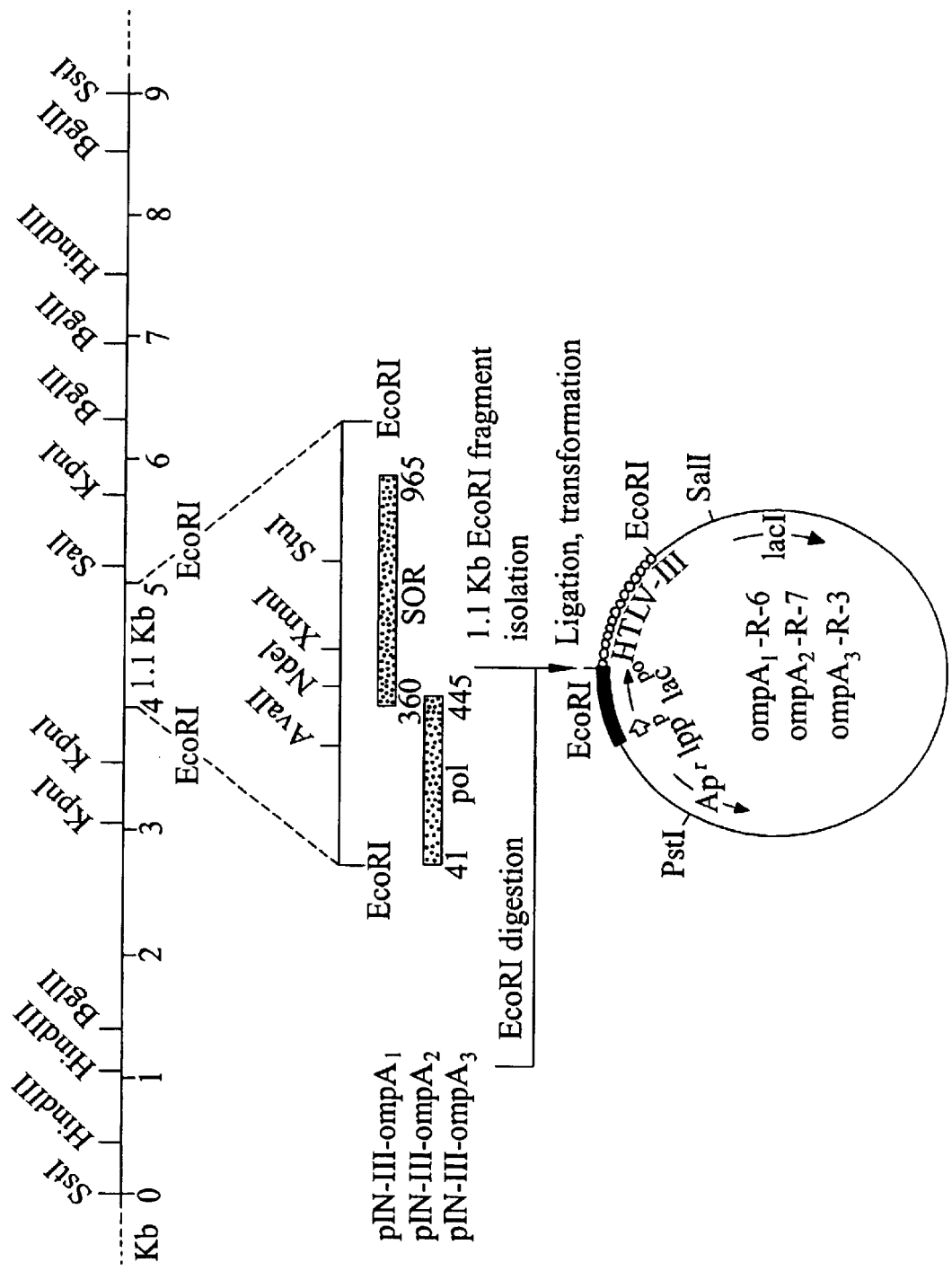
FIG. 4 shows sites at which the genome is cut by the restriction enzyme EcoRI and construction of recombinant plasmids carrying HTLV-III DNA.

Several gene segments that encode peptides showing immunoreactivity with anti-HTLV-III antibodies were demonstrated. Among these is a 1.1 Kb EcoRI restriction fragment. This fragment was inserted into ompA vectors in all three reading frames (FIG. 4). Cells were grown at 37° C. in L broth containing 100 μg/ml. ampicillin to an $OD_{600}$ of 0.2. At this time, the cell cultures were divided into two aliquots. IPTG was added to one aliquot to a final concentration of 2 mM (induced). IPTG was not added to the other aliquot (uninduced). Upon IPTG induction, transformants of all three plasmid constructs (designated $OmpA_1$-R-6 (O1R6), $OmpA_2$-R-7 (O2R7), and $OmpA_3$-R-3 (O3R3)) produced a 15 Kd peptide that is strongly reactive with anti-HTLV-III antibodies in sera from AIDS patients This reactivity is not detected when sera from normal individuals is used.

Figure 5:
FIG. 5 shows the nucleotide sequence of the ompA signal peptide and the pertinent region of recombinant plasmids ompA1-R-6; ompA2-R-7 and ompA3-R-3.

DNA sequence data of the HTLV-III genome indicates that there is an open reading frame inside the pol gene located at the 5'-end of the EcoRI fragment. DNA sequence analysis of the three recombinant constructs, O1R6, O2R7 and P3R3, confirmed that each of these recombinants has a different reading frame of the HTLV-III plus strand coupled to the coding sequence of each vector. Only in O3R3 is the reading frame of the inserted DNA in phase with that set by the signal peptide in the ompA vector; in O1R6 and O2R7 the pol gene segment DNA is out of phase (FIG. 5).

There is a 6 bp ribosome binding site, AAGGAG (Shine-Dalgarno sequence), located at nucleotide position 24–29 and an initiation codon, ATG, located 11 bp downstream (position 41–43). The 15 Kd peptide synthesized by all three recombinants appears to be translated from the transcripts using this internal initiation codon. If this is true, the peptide starts from the ATG located at position 41–43 and ends at the stop codon at position 446–448, producing a peptide of 135 amino acid residues encoded by the 3'-end segment of the pol gene of HTLV-III.

In addition to the 15 Kd peptide, the O3R3 construct, in which the reading frame of the HTLV-III DNA pol gene is in phase with that set by the vector, produced two additional peptides about 19 Kd and 16.5 Kd in size. It is possible that the 19 Kd peptide contains an additional 35 amino acid residues, 21 of which are from the signal peptide encoded by the ompA₃ vector and 14 encoded by the inserted HTLV-III DNA itself. The 16.5 Kd peptide may be the processed 19 Kd peptide in which the signal peptide is cleaved.

The O1R6 and O2R7 constructs also produce another peptide of about 17.5 Kd and weakly reactive with sera of AIDS patients. The origin of the peptide is not clear. The 1.1 Kb EcoRI fragment contains a second potential coding region designated as the short open reading frame (SOR) extending from nucleotide position 360 to 965 (FIG. 4). Four of the five AUG methionine codons in this region are near the 5'-end of this open reading frame. This DNA segment could encode peptides of 192, 185, 177 or 164 amino acid residues. However, there is no clearly recognizable ribosome binding site at the 5'-end of this open reading frame.

Further evidence also supports the conclusion that the 15 Kd peptide is indeed derived from the pol gene. First, deletion of the 3'-end StuI to EcoRI fragment from the 1.1 Kb EcoRI insert from O1R6, O2R7 and O3R8 (FIG. 4) does not affect the synthesis of the 15 Kd peptide. Second, clones containing only the 5'-end EcoRI to NdeI fragment still produce the same 16 Kd peptide. Finally, several recombinant clones containing various DNA fragments having the SOR coding sequence properly inserted into the open reading frame cloning vector, pMR100, produced lambdaCI-HTLV-III B-galactosidase tripartite fusion proteins which have very little immunoreactivity with anti-HTLV-III antibodies present in sera from AIDS patients.

Significant immunoreactivity against the 15 Kd peptide derived from the viral pol gene in sera from AIDS patients was detected. The identity of this immunoreactive peptide, with respect to the banding pattern of HTLV-III virion antigen in SDS-polyacrylamide gel electrophoresis, was determined by means of a competition inhibition immunoassay. Purified HTLV-III virions were treated with SDS, electrophoresed, and electroblotted onto a nitrocellulose filter. Identical filter strips containing disrupted HTLV-III virions were incubated with well characterized serum from an AIDS patient in the presence or absence of lysates of O1R6, O2R7, or control bacterial clones. The specific immunoreaction between anti-HTLV-III antibodies present in sera of the AIDS patients and the blotted virion proteins were then revealed by $^{125}$I-labeled goat anti-human antibody. Lysates of O1R6 block the immunoreactivity of the viral p31 protein with the AIDS serum, while lysates of control cells do not. This result suggests that the recombinant 16 Kd peptide encoded by 3'-end of the viral pol gene is also a part of another virion protein, p31, in contrast to the view shared by some that p31 is a cellular protein which co-purifies with HTLV-III virions.

The prevalence in the sera of AIDS patients of antibodies against the 15 Kd peptide was also evaluated. In Western blot analysis employing the lysate of O1R6 as the source of antigen, a panel of coded sera from AIDS patients and normal healthy individuals was tested. All of the 20 AIDS sera and none of the 8 normal controls reacted with the 15 Kd peptide. These data indicate that most, if not all, AIDS patients produce antibodies against the viral p31 protein.

EXAMPLE 6

Expression in *E. coli* of Open Reading Frame Gene Segments of HTLV-III

Figure 2:
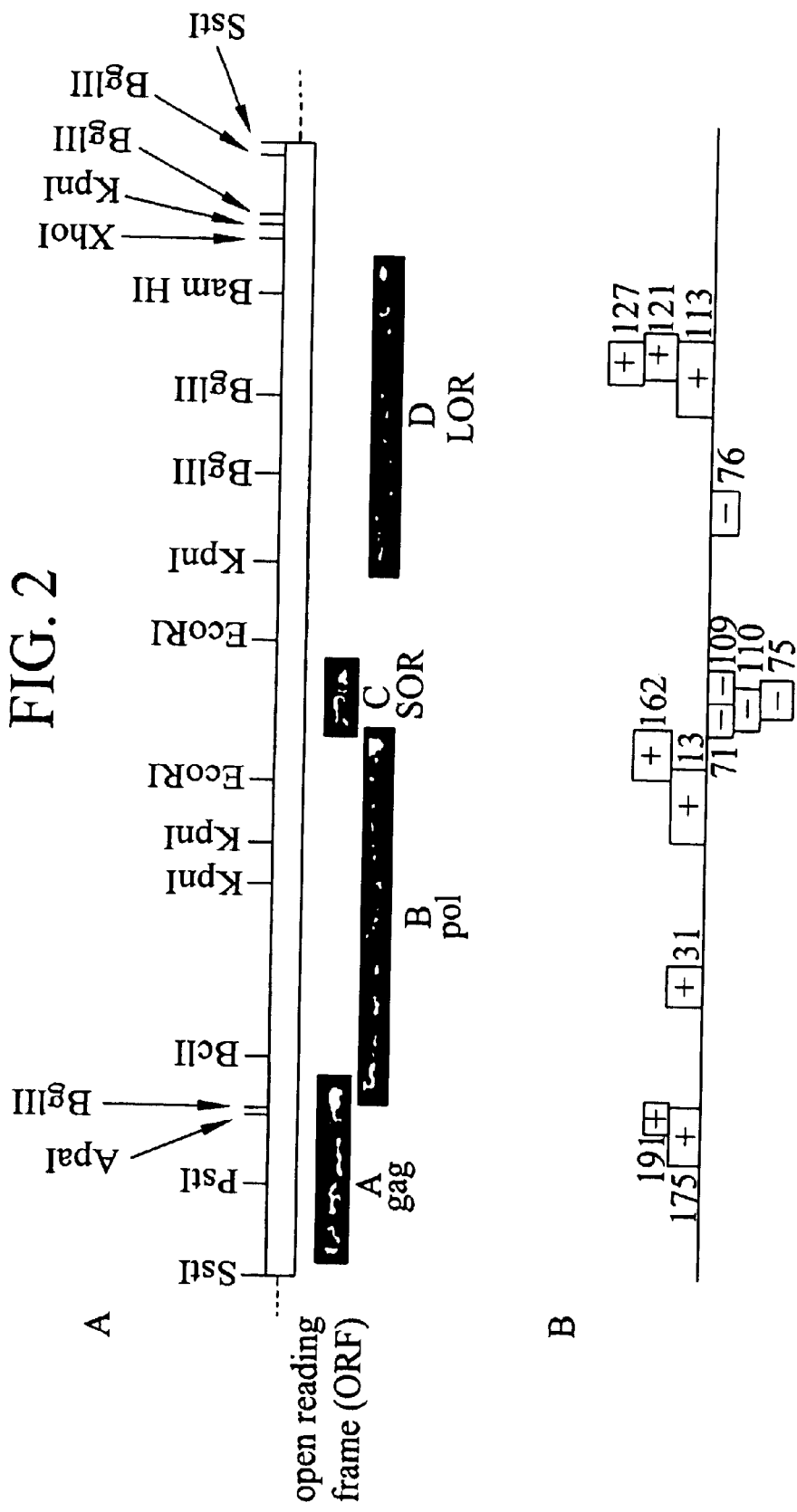
FIG. 2 is a representation of HTLV-III DNA.
Figure 6:
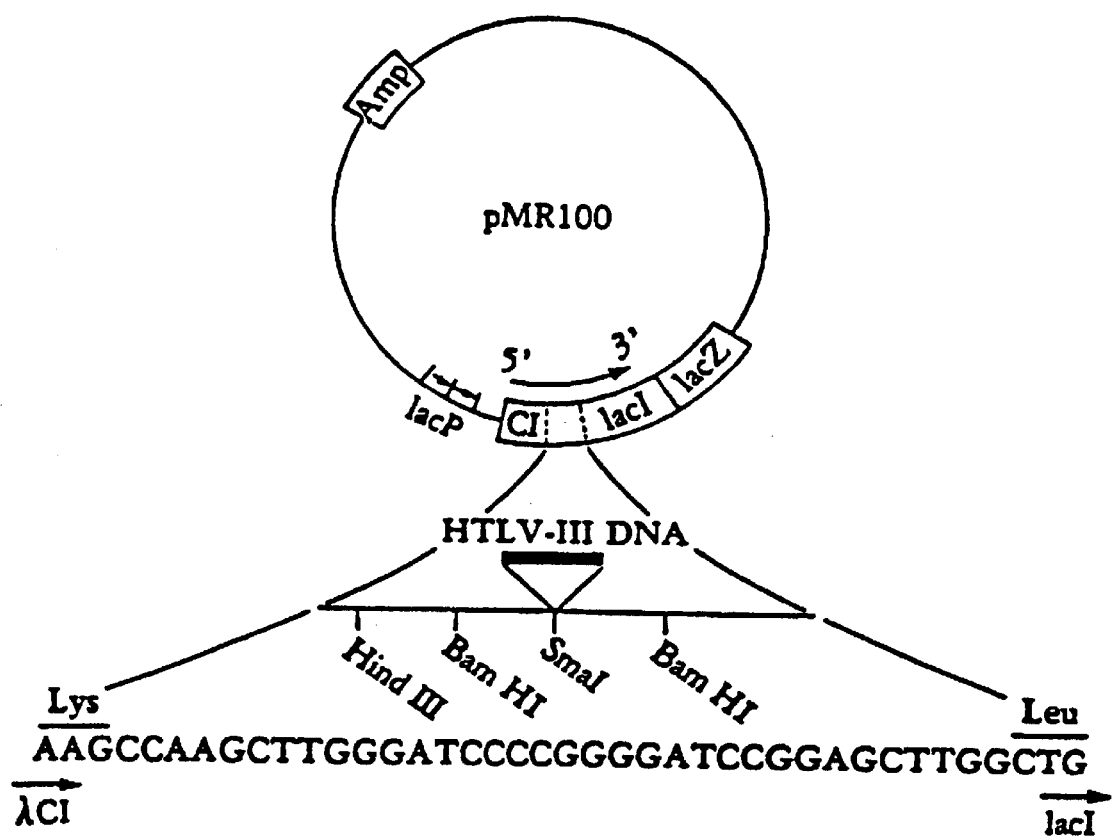
FIG. 6 represents the open reading frame expression vector pMR100 having HTLV-III DNA.
Figure 7:
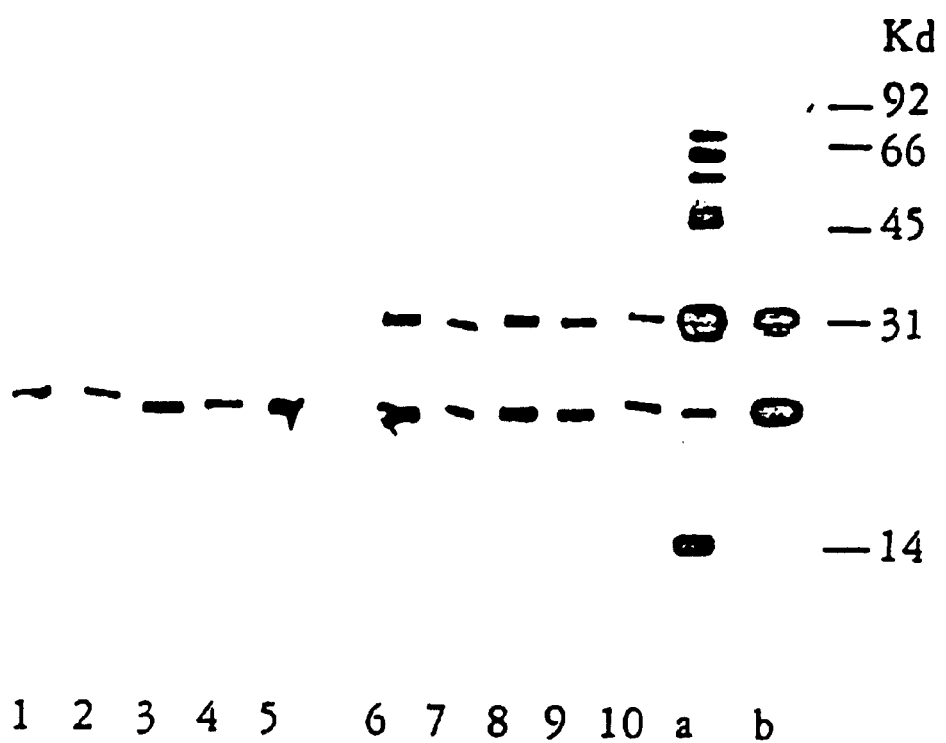
Figure 8:
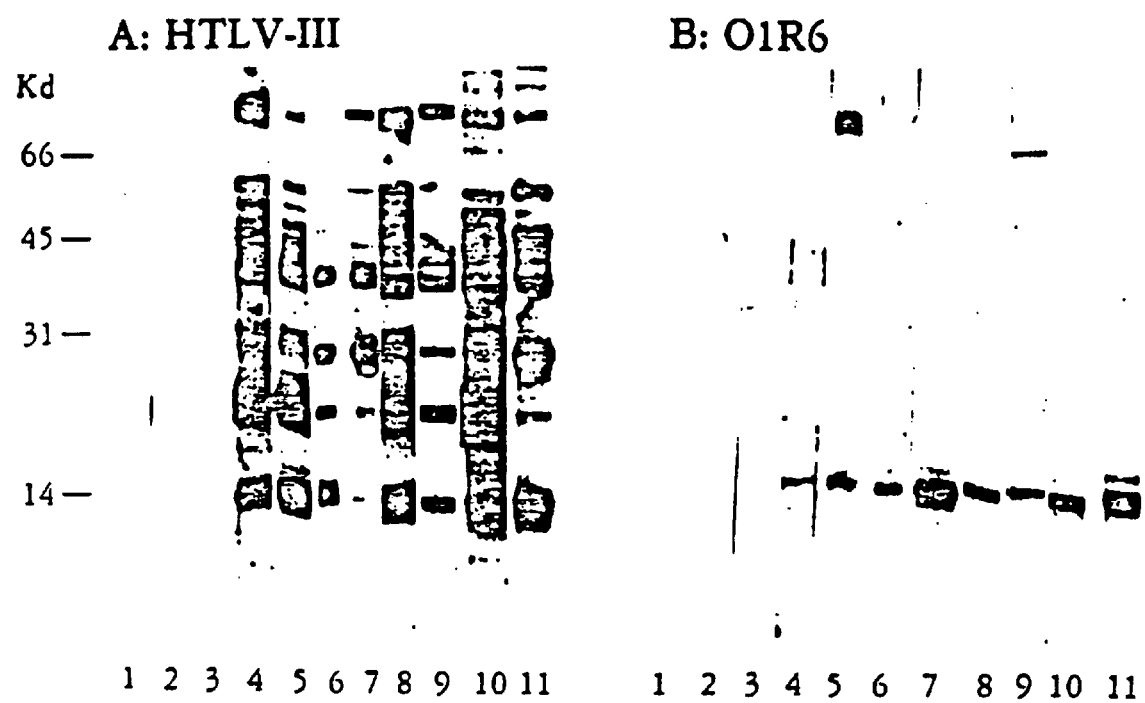
Figure 9:
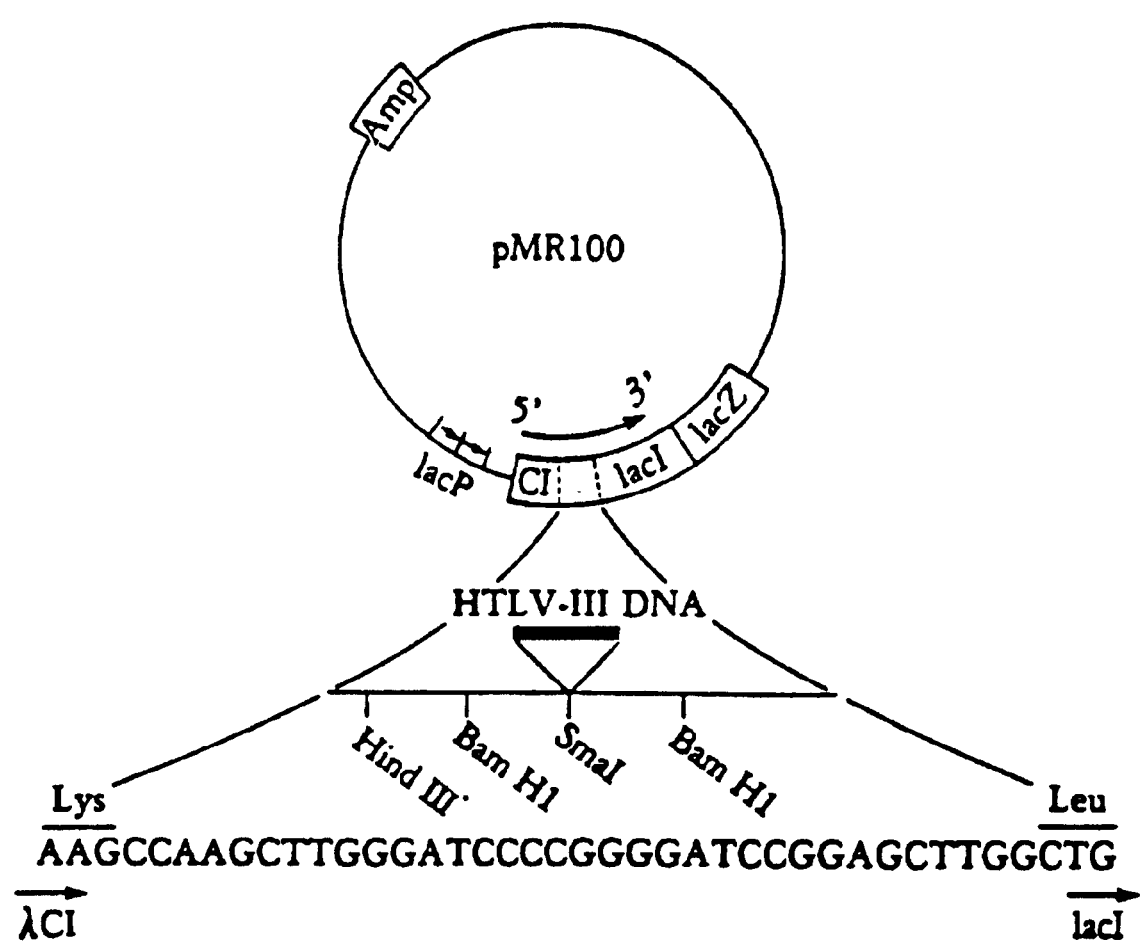
Figure 10:
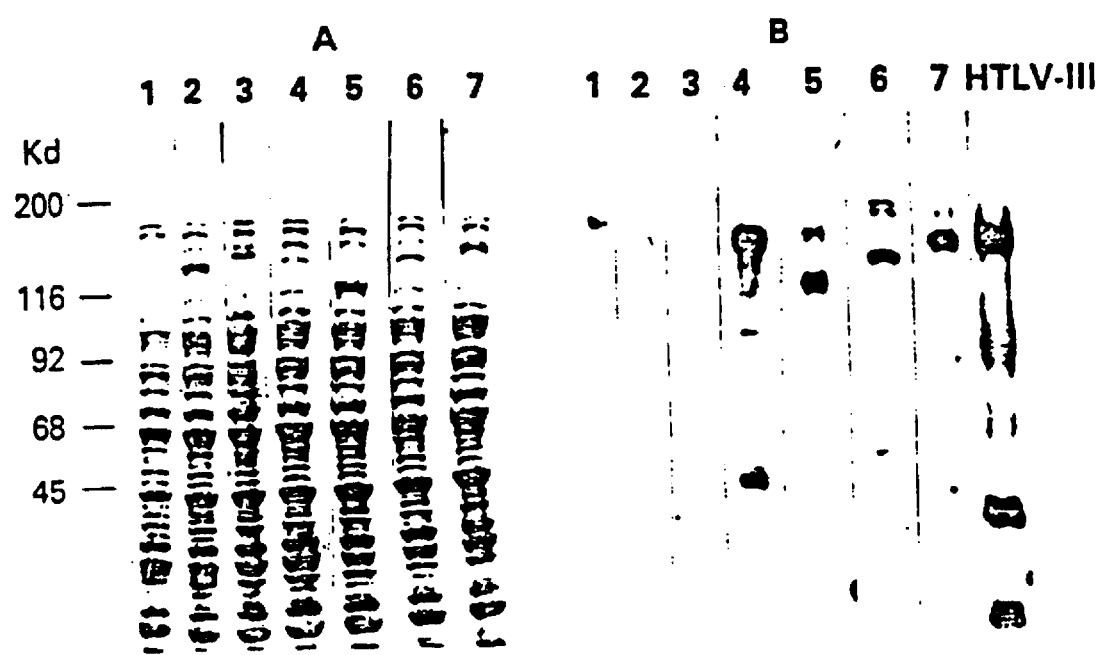

HTLV-III DNA was excised from lambda BH-10, which is a previously constructed recombinant lambda phage containing a 9 Kb segment of HTLV-III DNA inserted into the vector lambdagtwes lambda B (FIG. 2a). This HTLV-III DNA was sonicated and DNA fragments of about 0.5 Kb purified by gel electrophoresis, end repaired, and inserted into the SmaI site of the open reading frame (ORF) vector, pMR100 (FIG. 6). This vector contains a bacterial lac promoter DNA segment linked to a second DNA fragment containing a hybrid coding sequence in which the N-terminus (5' segment) of the lambda CI gene of bacteriophage lambda is fused to an N-terminal-deleted lacIZ gene (3' segment). A short linker DNA fragment, containing a SmaI cloning site, has been inserted between these two fragments in such a manner that a frame shift mutation has been introduced upstream of the lacIZ-coding DNA. As a result, pMR100 does not produce any detectable B-galactosidase activity when introduced into cells of the Lac⁻ host *E. coli* LG90. The insertion of foreign DNA containing an open reading frame, in this case the HTLV-III DNA, at the SmaI cloning site can reverse the frame shift mutation if the inserted coding sequence is in the correct reading frame with respect to both the lambdaCI leader and the lacIZ gene. Transformants were screened on MacConkey plates to detect individual clones that expressed β-galactosidase enzymatic activity in situ.

Among the 6000 ampicillin resistant transformants screened, about 300 were found to express B-galactosidase activity. Colony hybridization using $^{32}$p-labelled nick-translated HTLV-III DNA as a probe revealed that all these Lac⁺ clones contained HTLV-III DNA. In the Lac⁺ clones the HTLV-III fragment inserted into the Sma I site of pMR100 must contain no stop codons in the reading frame set by the lambdaCI leader segment and the lacIZ gene must also be in the correct translational reading frame. The three-element-fused genes were expressed as tripartite fusion proteins, having a portion of the lambdaCI protein at the N-terminus, the HTLV-III segment in the middle, and the lacIZ polypeptide at the C-terminus.

The proteins produced by the Lac⁺ clones were analyzed by resolving cell lysates on 7.5% SDS-polyacrylamide gels along with those of the control Lac⁺ clone pMR200, which produced a lambdaCI-β-galactosidase fusion protein. The lacIZ gene in pMR200 is identical to that in pMR100 except that it has a single base pair deletion which brings it in phase with the lambdaCI gene to produce an active β-galactosidase. By virtue of the very large size of the β-galactosidase and its fusion proteins, they are separated from the bulk of proteins in the cell lysates on the SDS-polyacrylamide gels and can be easily identified by Coomassie brilliant blue staining. Some of the Lac⁺ clones containing HTLV-III DNA produce polypeptides that are larger (15,000 to 27,000 daltons) than the lambdaCI-lacIZ fusion protein. These findings are consistent with data that the DNA inserts are up to 700 bp long. The β-galactosidase fusion proteins accounted for about 1–2% of total cellular protein.

The peptides produced by the Lac⁺ clones were examined by Western blot analysis for immunoreactivity with sera from AIDS patients. After the lysates of Lac⁺ clones were electrophoresed in SDS-polyacrylamide gels, they were electro-transferred to nitrocellulose filters. These protein blots were first reacted with AIDS patient sera and then with $^{125}$I-labeled goat anti-human IgG. The recombinant peptides also reacted with anti-B-galactosidase antiserum, consistent with the proposition that they had the general structure lambdaCI-HTLV-III peptide-LacIZ. From the immunoreactivity pattern of the negative controls, pMR100 and pMR200, which do not contain an HTLV-III DNA insert, it is evident that this particular AIDS serum contains antibodies reactive with several bacterial proteins of the host *E. coli*. This is not surprising, since AIDS patients are usually infected with a number of bacteria. Absorbing AIDS patient sera with Sepharose 4B conjugated with *E. coli* extract reduced the background immunoreactivity to some extent but did not completely eliminate it.

About 300 independent HTLV-III DNA-containing Lac$^+$ colonies were analyzed in SDS polyacrylamide gels using Coomassie brilliant blue staining and Western blotting. About half of them were found to express fusion proteins containing extra peptides of about 100–200 amino acids, corresponding to DNA inserts of 300–600 bp long. Of these fusion proteins, 20 were found to react specifically with sera from AIDS patients. The unreactive clones probably contain peptides that fold in such a way that they are not reactive with antibodies or correspond to regions of HTLV-III protein molecules which are not immunogenic in AIDS patients. The other half of the Lac$^+$ clones expressed fusion proteins whose sizes were not obviously different from that of the lambdaCI B-galactosidase protein. None from this group of fusion proteins was found to react with sera from AIDS patients.

The HTLV-III DNA inserts from Lac$^+$ ORF clones were mapped to specific segments in the HTLV-III genome using Southern blotting procedures. In these studies, each plasmid clone was labelled with $^{32}$P by nick-translation and hybridized to a battery of HTLV-III DNA restriction fragments. This hybridization analysis mapped all of the Lac$^+$ ORF clones into four open reading frame segments designated ORF-A, ORF-B, ORF-C, and ORF-D (FIG. 2a) consistent with the DNA sequencing data. The open reading frames ORF-A and -B, corresponding to the coding regions of the gag and pol genes, are 1.5 Kb and 3.0 Kb long, respectively. ORF-C is about 0.6 Kb long, slightly overlaps with the ORF-B region, and is capable of encoding a polypeptide of 21 overlaps with the ORF-B region, and is capable of encoding a polypeptide of 21 Kd. The location of ORF-C and its overlap with the pol gene are reminiscent of the structure of the env genes in HTLV-I and -II. However, ORF-C, designated as the short open reading frame (sor), is too short to code for the entire envelope protein. The fourth open reading frame, ORF-D, is 2.5 Kb long and could encode both a large precursor of the major envelope glycoprotein and another protein derived from the 3' terminus, which may be analogous to the lor products of HTLV-I and -II. This gene region of HTLV-III, designated env-lor, is at least twice as long as the lor of HTLV-I and HTLV-II and it is presently unclear whether single or multiple proteins are encoded herein.

Both Southern blotting and DNA sequencing studies were employed to analyze a number of clones. As shown in FIG. 2b, the Lac$^+$ ORF clones expressing fusion proteins immunoreactive with sera from AIDS patients were located in ORF-A (e.g. #175 and #191), ORF-B (e.g. #13, 31, and 162), or ORF-D (e.g. #113, 121, and 127) and not in the sor region. Not all peptides in these regions were immunoreactive, e.g. ORF clone #76 located in ORF-D.

Analysis of the open reading frame structures in HTLV-III posed questions as to which open reading frame(s) corresponds to the env gene. It is possible that the env-lor region in HTLV-III contains all or a part of the env gene in addition to the presumed lor gene. Recent evidence suggests that the lor in HTLV-I encodes a 42 Kd protein involved in the process of viral activation and transformation. When the lysate of one of the ORF clones (#127 in FIG. 2b) was tested against sera from 20 AIDS patients and 12 healthy normals in a strip radioimmunoassay based on the Western blot technique, immunoreactivity against the lambdaCI-HTLV-III-B-galactosidase fusion polypeptide was detected in the sera from 19 of the AIDS patients and none from normal controls. This result indicates that the protein encoded by the portion of the env-lor region contained in ORF clone #127 is produced in HTLV-III infected cells and induces antibody production in most if not all AIDS patients.

Industrial Applicability

This invention has industrial applicability in screening for the presence of HTLV-III DNA in body fluids and the diagnosis of AIDS.

Equivalents

Those skilled in the art will recognize, or be able to ascertain, using no more than routine experimentation, numerous equivalents to the specific substances and procedures described herein. Such equivalents are considered to be within the scope of this invention and are covered by the following claims.

What is claimed is:

1. An isolated HIV-1 RNA comprising (i) the gag open reading frame consisting of nucleotides 113–1648 of SEQ ID NO: 4 or nucleotides 111–1646 of SEQ ID NO: 5, or (ii) the gag open reading frame encoding, SEQ ID NO: 8.

2. An isolated HIV-1 RNA comprising (i) the pol open reading frame consisting of nucleotides 1408–4452 of SEQ ID NO: 4 or nucleotides 1406–4450 of SEQ ID NO: 5, or (ii) the pol open reading frame encoding SEQ ID NO: 9.

3. An isolated HIV-1 RNA comprising (i) the sor open reading frame consisting of nucleotides 4367–4975 of SEQ ID NO: 4 or nucleotides 4365–4973 of SEQ ID NO: 5, or (ii) the sor open reading frame encoding SEQ ID NO: 10.

4. An isolated HIV-1 RNA comprising (i) the env or env-lor open reading frame consisting of nucleotides 5560–8148 of SEQ ID NO: 4, or nucleotides 205–2776 of SEQ ID NO: 6, or (ii) the env or env-lor open reading frame encoding SEQ ID NO: 11.

5. A diagnostic means comprising said isolated HIV-1 RNA according to claim 1 for detecting HIV-1 in body fluids.

6. A diagnostic means comprising said isolated HIV-1 RNA according to claim 2 for detecting HIV-1 in body fluids.

7. A diagnostic means comprising said isolated HIV-1 RNA according to claim 3 for detecting HIV-1 in body fluids.

8. A diagnostic means comprising said isolated HIV-1 RNA according to claim 4 for detecting HIV-1 in body fluids.

9. A fragment of the isolated HIV-1 RNA of claim 1 comprising at least 20 contiguous nucleotides of nucleotides 113–1648 of SEQ ID NO: 4 or nucleotides 111–1646 of SEQ ID NO: 5 or at least 200 contiguous nucleotides encoding SEQ ID NO: 8.

10. A fragment of the isolated HIV-1 RNA of claim 2 comprising at least 20 contiguous nucleotides of nucleotides 1408–4452 of SEQ ID NO: 4 or nucleotides 1406–4450 of SEQ ID NO: 5 or at least 200 contiguous nucleotides encoding SEQ ID NO: 9.

11. A fragment of the isolated HIV-1 RNA of claim 3 comprising at least 20 contiguous nucleotides of nucleotides 4367–4975 of SEQ ID NO: 4 or nucleotides 4365–4973 of SEQ ID NO: 5 or at least 200 contiguous nucleotides encoding SEQ ID NO: 10.

12. A fragment of the isolated HIV-1 RNA of claim 4 comprising at least 20 contiguous nucleotides of nucleotides 5560–8148 of SEQ ID NO: 4 or nucleotides 205–2776 of SEQ ID NO: 6 or at least 200 contiguous nucleotides encoding SEQ ID NO: 11.

13. A diagnostic means comprising the fragment of claim 9.

14. A diagnostic means comprising the fragment of claim 10.

15. A diagnostic means comprising the fragment of claim 11.

16. A diagnostic means comprising the fragment of claim 12.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 492 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (vi) ORIGINAL SOURCE:
      (A) ORGANISM: HTLV-III (ix) FEATURE:

(A) NAME/KEY: misc_feature
            (B) LOCATION: 1..492
            (D) OTHER INFORMATION: /standard_name= "Clone BH10"
                /note= "Corresponds to nucleotide positions -453
                to 39 in figure 3 of US 06/693,866 (parent)"

(xi) SEQUENCE DESCRIPTION: SEQ ID NO:1:

TGGAAGGGCT AATTCACTCC CAACGAAGAC AAGATATCCT TGATCTGTGG ATCTACCACA        60

CACAAGGCTA CTTCCCTGAT TAGCAGAACT ACACACCAGG GCCAGGGATC AGATATCCAC       120

TGACCTTTGG ATGGTGCTAC AAGCTAGTAC CAGTTGAGCC AGAGAAGTTA GAAGAAGCCA       180

ACAAAGGAGA GAACACCAGC TTGTTACACC CTGTGAGCCT GCATGGAATG GATGACCCGG       240

AGAGAGAAGT GTTAGAGTGG AGGTTTGACA GCCGCCTAGC ATTTCATCAC ATGGCCCGAG       300

AGCTGCATCC GGAGTACTTC AAGAACTGCT GACATCGAGC TTGCTACAAG GGACTTTCCG       360

CTGGGGACTT TCCAGGGAGG CGTGGCCTGG GCGGGACTGG GGAGTGGCGA GCCCTCAGAT       420

CCTGCATATA AGCAGCTGCT TTTTGCCTGT ACTGGGTCTC TCTGGTTAGA CCAGATCTGA       480

GCCTGGGAGC TC                                                          492

(2) INFORMATION FOR SEQ ID NO:2:

(i) SEQUENCE CHARACTERISTICS:
        (A) LENGTH: 492 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: HTLV-III (ix) FEATURE:
        (A) NAME/KEY: misc_feature
        (B) LOCATION: 1..492
        (D) OTHER INFORMATION: /standard_name= "Clone BH8"
            /note= "Corresponds to nucleotide positions -453
            to 39 in figure 3 of US 06/693,866 (parent)"

(xi) SEQUENCE DESCRIPTION: SEQ ID NO:2:

TGGAAGGGCT AATTCACTCC CAACGAAGAC AAGATATCCT TGATCTGTGG ATCCACCACA        60

CACAAGGCTA CTTCCCTGAT TGGCAGAACT ACACACCAGG GCCAGGAGTC AGATATCCAC       120

TGACCTTTGG ATGGTGCTAC AAGCTAGTAC CAGTTGAGCC AGAGAAGTAA GAAGAAGCCA       180

ATAAAGGAGA GAACACCAGC TTGTTACACC CTGTGAGCCT GCATGGAATG GATGACCCTG       240

AGAGAGAAGT GTTAGAGTGG AGGTTTGACA GCCGCCTAGC ATTTCATCAC ATGGCCCGAG       300

AGCTGCATCC GGAGTACTTC AAGAACTGCT GATATCGAGC TTGCTACAAG GGACTTTCCG       360

CTGGGGACTT TCCAGGGAGG CGTGGCCTGG GCGGGACTGG GGAGTGGCGA GCCCTCAGAT       420

CCTGCATATA AGCAGCTGCT TTTTGCCTGT ACTGGGTCTC TCTGGTTAGA CCAGATCTGA       480

GCCTGGGAGC TC                                                          492

(2) INFORMATION FOR SEQ ID NO:3:

(i) SEQUENCE CHARACTERISTICS:
        (A) LENGTH: 182 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
             (A) ORGANISM: HTLV-III (ix) FEATURE:
             (A) NAME/KEY: misc_feature
             (B) LOCATION: 1..182
             (D) OTHER INFORMATION: /standard_name= "Clone HXB2"
                 /note= "Corresponds to nucleotide positions 40 to
                 221 in figure 3 of US 06/693,866 (parent)"

(xi) SEQUENCE DESCRIPTION: SEQ ID NO:3:

TCTGGCTAAC TAGGGAACCC ACTGCTTAAG CCTCAATAAA GCTTGCCTTG AGTGCTTCAA        60

GTAGTGTGTG CCCGTCTGTT GTGTGACTCT GGTAACTAGA GATCCCTCAG ACCCTTTTAG       120

TCAGTGTGGA AAATCTCTAG CAGTGGCGCC CGAACAGGGA CCTGAAAGCG AAAGGGAAAC      180

CA                                                                      182

(2) INFORMATION FOR SEQ ID NO:4:

(i) SEQUENCE CHARACTERISTICS:
             (A) LENGTH: 8933 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (vi) ORIGINAL SOURCE:
             (A) ORGANISM: HTLV-III (ix) FEATURE:
             (A) NAME/KEY: misc_feature
             (B) LOCATION: 1..8933
             (D) OTHER INFORMATION: /standard_name= "Clone BH10"
                 /note= "Corresponds to nucleotide positions 222 to
                 9154 in figure 3 of EP 85307260"

(ix) FEATURE:
             (A) NAME/KEY: mat_peptide
             (B) LOCATION: 113..1648
             (D) OTHER INFORMATION: /product= "gag"

(ix) FEATURE:
             (A) NAME/KEY: mat_peptide
             (B) LOCATION: 1408..4452
             (D) OTHER INFORMATION: /product= "pol"

(ix) FEATURE:
             (A) NAME/KEY: mat_peptide
             (B) LOCATION: 4367..4975
             (D) OTHER INFORMATION: /product= "sor"

(ix) FEATURE:
             (A) NAME/KEY: mat_peptide
             (B) LOCATION: 5560..8148
             (D) OTHER INFORMATION: /product= "env"

(xi) SEQUENCE DESCRIPTION: SEQ ID NO:4:

GAGCTCTCTC GACGCAGGAC TCGGCTTGCT GAAGCGCGCA CGGCAAGAGG CGAGGGGCGG        60

CGACTGGTGA GTACGCCAAA AATTTTGACT AGCGGAGGCT AGAAGGAGAG AGATGGGTGC       120

GAGAGCGTCA GTATTAAGCG GGGGAGAATT AGATCGATGG GAAAAAATTC GGTTAAGGCC       180

AGGGGGAAAG AAAAAATATA AATTAAAACA TATAGTATGG GCAAGCAGGG AGCTAGAACG       240

ATTCGCAGTT AATCCTGGCC TGTTAGAAAC ATCAGAAGGC TGTAGACAAA TACTGGGACA       300

GCTACAACCA TCCCTTCAGA CAGGATCAGA AGAACTTAGA TCATTATATA ATACAGTAGC       360

```
AACCCTCTAT TGTGTGCATC AAAGGATAGA GATAAAAGAC ACCAAGGAAG CTTTAGACAA      420

GATAGAGGAA GAGCAAAACA AAAGTAAGAA AAAAGCACAG CAAGCAGCAG CTGACACAGG      480

ACACAGCAGT CAGGTCAGCC AAAATTACCC TATAGTGCAG AACATCCAGG GGCAAATGGT      540

ACATCAGGCC ATATCACCTA GAACTTTAAA TGCATGGGTA AAAGTAGTAG AAGAGAAGGC      600

TTTCAGCCCA GAAGTAATAC CCATGTTTTC AGCATTATCA GAAGGAGCCA CCCCACAAGA      660

TTTAAACACC ATGCTAAACA CAGTGGGGGG ACATCAAGCA GCCATGCAAA TGTTAAAAGA      720

GACCATCAAT GAGGAAGCTG CAGAATGGGA TAGAGTACAT CCAGTGCATG CAGGGCCTAT      780

TGCACCAGGC CAGATGAGAG AACCAAGGGG AAGTGACATA GCAGGAACTA CTAGTACCCT      840

TCAGGAACAA ATAGGATGGA TGACAAATAA TCCACCTATC CCAGTAGGAG AAATTTATAA      900

AAGATGGATA ATCCTGGGAT TAAATAAAAT AGTAAGAATG TATAGCCCTA CCAGCATTCT      960

GGACATAAGA CAAGGACCAA AGAACCTTTT TAGAGACTAT GTAGACCGGT TCTATAAAAC     1020

TCTAAGAGCC GAGCAAGCTT CACAGGAGGT AAAAAATTGG ATGACAGAAA CCTTGTTGGT     1080

CCAAAATGCG AACCCAGATT GTAAGACTAT TTTAAAAGCA TTGGGACCAG CGGCTACACT     1140

AGAAGAAATG ATGACAGCAT GTCAGGGAGT AGGAGGACCC GGCCATAAGG CAAGAGTTTT     1200

GGCTGAAGCA ATGAGCCAAG TAACAAATAC AGCTACCATA ATGATGCAGA GAGGCAATTT     1260

TAGGAACCAA AGAAAGATGG TTAAGTGTTT CAATTGTGGC AAAGAAGGGC ACACAGCCAG     1320

AAATTGCAGG GCCCCTAGGA AAAAGGGCTG TTGGAAATGT GGAAAGGAAG GACACCAAAT     1380

GAAAGATTGT ACTGAGAGAC AGGCTAATTT TTTAGGGAAG ATCTGGCCTT CCTACAAGGG     1440

AAGGCCAGGG AATTTTCTTC AGAGCAGACC AGAGCCAACA GCCCCACCAT TCCTTCAGAG     1500

CAGACCAGAG CCAACAGCCC CACCAGAAGA GAGCTTCAGG TCTGGGGTAG AGACAACAAC     1560

TCCCCCTCAG AAGCAGGAGC CGATAGACAA GGAACTGTAT CCTTTAACTT CCCTCAGATC     1620

ACTCTTTGGC AACGACCCCT CGTCACAATA AAGATAGGGG GGCAACTAAA GGAAGCTCTA     1680

TTAGATACAG GAGCAGATGA TACAGTATTA GAAGAAATGA GTTTGCCAGG AAGATGGAAA     1740

CCAAAAATGA TAGGGGGAAT TGGAGGTTTT ATCAAAGTAA GACAGTATGA TCAGATACTC     1800

ATAGAAATCT GTGGACATAA AGCTATAGGT ACAGTATTAG TAGGACCTAC ACCTGTCAAC     1860

ATAATTGGAA GAAATCTGTT GACTCAGATT GGTTGCACTT TAAATTTTCC CATTAGCCCT     1920

ATTGAGACTG TACCAGTAAA ATTAAAGCCA GGAATGGATG GCCCAAAAGT TAAACAATGG     1980

CCATTGACAG AAGAAAAAAT AAAAGCATTA GTAGAAATTT GTACAGAAAT GGAAAAGGAA     2040

GGGAAAATTT CAAAAATTGG GCCTGAGAAT CCATACAATA CTCCAGTATT TGCCATAAAG     2100

AAAAAAGACA GTACTAAATG GAGAAAATTA GTAGATTTCA GAGAACTTAA TAAGAGAACT     2160

CAAGACTTCT GGGAAGTTCA ATTAGGAATA CCACATCCCG CAGGGTTAAA AAGAAAAAA      2220

TCAGTAACAG TACTGGATGT GGGTGATGCA TATTTTTCAG TTCCCTTAGA TGAAGACTTC     2280

AGGAAGTATA CTGCATTTAC CATACCTAGT ATAAACAATG AGACACCAGG GATTAGATAT     2340

CAGTACAATG TGCTTCCACA GGGATGGAAA GGATCACCAG CAATATTCCA AGTAGCATG      2400

ACAAAAATCT TAGAGCCTTT TAAAAAACAA AATCCAGACA TAGTTATCTA TCAATACATG     2460

GATGATTTGT ATGTAGGATC TGACTTAGAA ATAGGGCAGC ATAGAACAAA AATAGAGGAG     2520

CTGAGACAAC ATCTGTTGAG GTGGGGACTT ACCACACCAG ACAAAAAACA TCAGAAAGAA     2580

CCTCCATTCC TTTGGATGGG TTATGAACTC CATCCTGATA AATGGACAGT ACAGCCTATA     2640

GTGCTGCCAG AAAAAGACAG CTGGACTGTC AATGACATAC AGAAGTTAGT GGGGAAATTG     2700
```

```
AATTGGGCAA GTCAGATTTA CCCAGGGATT AAAGTAAGGC AATTATGTAA ACTCCTTAGA     2760

GGAACCAAAG CACTAACAGA AGTAATACCA CTAACAGAAG AAGCAGAGCT AGAACTGGCA     2820

GAAAACAGAG AGATTCTAAA AGAACCAGTA CATGGAGTGT ATTATGACCC ATCAAAAGAC     2880

TTAATAGCAG AAATACAGAA GCAGGGGCAA GGCCAATGGA CATATCAAAT TTATCAAGAG     2940

CCATTTAAAA ATCTGAAAAC AGGAAAATAT GCAAGAATGA GGGGTGCCCA CACTAATGAT     3000

GTAAAACAAT TAACAGAGGC AGTGCAAAAA ATAACCACAG AAAGCATAGT AATATGGGGA     3060

AAGACTCCTA AATTTAAACT ACCCATACAA AAGGAAACAT GGGAAACATG GTGGACAGAG     3120

TATTGGCAAG CCACCTGGAT TCCTGAGTGG GAGTTTGTTA ATACCCCTCC TTTAGTGAAA     3180

TTATGGTACC AGTTAGAGAA AGAACCCATA GTAGGAGCAG AAACCTTCTA TGTAGATGGG     3240

GCAGCTAACA GGGAGACTAA ATTAGGAAAA GCAGGATATG TTACTAACAA AGGAAGACAA     3300

AAGGTTGTCC CCCTAACTAA CACAACAAAT CAGAAAACTG AGTTACAAGC AATTTATCTA     3360

GCTTTGCAGG ATTCAGGATT AGAAGTAAAC ATAGTAACAG ACTCACAATA TGCATTAGGA     3420

ATCATTCAAG CACAACCAGA TAAAAGTGAA TCAGAGTTAG TCAATCAAAT AATAGAGCAG     3480

TTAATAAAAA AGGAAAAGGT CTATCTGGCA TGGGTACCAG CACACAAAGG AATTGGAGGA     3540

AATGAACAAG TAGATAAATT AGTCAGTGCT GGAATCAGGA AAATACTATT TTTAGATGGA     3600

ATAGATAAGG CCCAAGATGA ACATGAGAAA TATCACAGTA ATTGGAGAGC AATGGCTAGT     3660

GATTTTAACC TGCCACCTGT AGTAGCAAAA GAAATAGTAG CCAGCTGTGA TAAATGTCAG     3720

CTAAAAGGAG AAGCCATGCA TGGACAAGTA GACTGTAGTC CAGGAATATG GCAACTAGAT     3780

TGTACACATT TAGAAGGAAA AGTTATCCTG GTAGCAGTTC ATGTAGCCAG TGGATATATA     3840

GAAGCAGAAG TTATTCCAGC AGAAACAGGG CAGGAAACAG CATATTTTCT TTTAAAATTA     3900

GCAGGAAGAT GGCCAGTAAA AACAATACAT ACAGACAATG GCAGCAATTT CACCAGTGCT     3960

ACGGTTAAGG CCGCCTGTTG GTGGGCGGGA ATCAAGCAGG AATTTGGAAT TCCCTACAAT     4020

CCCCAAAGTC AAGGAGTAGT AGAATCTATG AATAAAGAAT TAAAGAAAAT TATAGGACAG     4080

GTAAGAGATC AGGCTGAACA TCTTAAGACA GCAGTACAAA TGGCAGTATT CATCCACAAT     4140

TTTAAAAGAA AAGGGGGGAT TGGGGGGTAC AGTGCAGGGG AAAGAATAGT AGACATAATA     4200

GCAACAGACA TACAAACTAA AGAATTACAA AAACAAATTA CAAAAATTCA AAATTTTCGG     4260

GTTTATTACA GGGACAGCAG AAATCCACTT TGGAAAGGAC CAGCAAAGCT CCTCTGGAAA     4320

GGTGAAGGGG CAGTAGTAAT ACAAGATAAT AGTGACATAA AAGTAGTGCC AAGAAGAAAA     4380

GCAAAGATCA TTAGGGATTA TGGAAAACAG ATGGCAGGTG ATGATTGTGT GGCAAGTAGA     4440

CAGGATGAGG ATTAGAACAT GGAAAAGTTT AGTAAAACAC CATATGTATG TTTCAGGGAA     4500

AGCTAGGGGA TGGTTTTATA GACATCACTA TGAAAGCCCT CATCCAAGAA TAAGTTCAGA     4560

AGTACACATC CCACTAGGGG ATGCTAGATT GGTAATAACA ACATATTGGG GTCTGCATAC     4620

AGGAGAAAGA GACTGGCATT TGGGTCAGGG AGTCTCCATA GAATGGAGGA AAAAGAGATA     4680

TAGCACACAA GTAGACCCTG AACTAGCAGA CCAACTAATT CATCTGTATT ACTTTGACTG     4740

TTTTTCAGAC TCTGCTATAA GAAAGGCCTT ATTAGGACAC ATAGTTAGCC CTAGGTGTGA     4800

ATATCAAGCA GGACATAACA AGGTAGGATC TCTACAATAC TTGGCACTAG CAGCATTAAT     4860

AACACCAAAA AAGATAAAGC CACCTTTGCC TAGTGTTACG AAACTGACAG AGGATAGATG     4920

GAACAAGCCC CAGAAGACCA AGGGCCACAG AGGGAGCCAC ACAATGAATG GACACTAGAG     4980

CTTTTAGAGG AGCTTAAGAA TGAAGCTGTT AGACATTTTC CTAGGATTTG GCTCCATGGC     5040

TTAGGGCAAC ATATCTATGA AACTTATGGG GATACTTGGG CAGGAGTGGA AGCCATAATA     5100
```

```
AGAATTCTGC AACAACTGCT GTTTATCCAT TTTCAGAATT GGGTGTCGAC ATAGCAGAAT    5160

AGGCGTTACT CGACAGAGGA GAGCAAGAAA TGGAGCCAGT AGATCCTAGA CTAGAGCCCT    5220

GGAAGCATCC AGGAAGTCAG CCTAAAACTG CTTGTACCAA TTGCTATTGT AAAAAGTGTT    5280

GCTTTCATTG CCAAGTTTGT TTCATAACAA AAGCCTTAGG CATCTCCTAT GGCAGGAAGA    5340

AGCGGAGACA GCGACGAAGA CCTCCTCAAG GCAGTCAGAC TCATCAAGTT TCTCTATCAA    5400

AGCAGTAAGT AGTACATGTA ATGCAACCTA TACAAATAGC AATAGTAGCA TTAGTAGTAG    5460

CAATAATAAT AGCAATAGTT GTGTGGTCCA TAGTAATCAT AGAATATAGG AAAATATTAA    5520

GACAAAGAAA AATAGACAGG TTAATTGATA GACTAATAGA AAGAGCAGAA GACAGTGGCA    5580

ATGAGAGTGA AGGAGAAATA TCAGCACTTG TGGAGATGGG GGTGGAGATG GGCACCATG     5640

CTCCTTGGGA TGTTGATGAT CTGTAGTGCT ACAGAAAAAT TGTGGGTCAC AGTCTATTAT    5700

GGGGTACCTG TGTGGAAGGA AGCAACCACC ACTCTATTTT GTGCATCAGA TGCTAAAGCA    5760

TATGATACAG AGGTACATAA TGTTTGGGCC ACACATGCCT GTGTACCCAC AGACCCCAAC    5820

CCACAAGAAG TAGTATTGGT AAATGTGACA GAAAATTTTA ACATGTGGAA AAATGACATG    5880

GTAGAACAGA TGCATGAGGA TATAATCAGT TTATGGGATC AAAGCCTAAA GCCATGTGTA    5940

AAATTAACCC CACTCTGTGT TAGTTTAAAG TGCACTGATT TGAAGAATGA TACTAATACC    6000

AATAGTAGTA GCGGGAGAAT GATAATGGAG AAAGGAGAGA TAAAAAACTG CTCTTTCAAT    6060

ATCAGCACAA GCATAAGAGG TAAGGTGCAG AAAGAATATG CATTTTTTTA TAAACTTGAT    6120

ATAATACCAA TAGATAATGA TACTACCAGC TATACGTTGA CAAGTTGTAA CACCTCAGTC    6180

ATTACACAGG CCTGTCCAAA GGTATCCTTT GAGCCAATTC CCATACATTA TTGTGCCCCG    6240

GCTGGTTTTG CGATTCTAAA ATGTAATAAT AAGACGTTCA ATGGAACAGG ACCATGTACA    6300

AATGTCAGCA CAGTACAATG TACACATGGA ATTAGGCCAG TAGTATCAAC TCAACTGCTG    6360

TTAAATGGCA GTCTGGCAGA AGAAGAGGTA GTAATTAGAT CTGCCAATTT CACAGACAAT    6420

GCTAAAACCA TAATAGTACA GCTGAACCAA TCTGTAGAAA TTAATTGTAC AAGACCCAAC    6480

AACAATACAA GAAAAAGTAT CCGTATCCAG AGAGGACCAG GGAGAGCATT TGTTACAATA    6540

GGAAAAATAG GAAATATGAG ACAAGCACAT TGTAACATTA GTAGAGCAAA ATGGAATAAC    6600

ACTTTAAAAC AGATAGATAG CAAATTAAGA GAACAATTTG GAAATAATAA AACAATAATC    6660

TTTAAGCAGT CCTCAGGAGG GGACCCAGAA ATTGTAACGC ACAGTTTTAA TTGTGGAGGG    6720

GAATTTTTCT ACTGTAATTC AACACAACTG TTTAATAGTA CTTGGTTTAA TAGTACTTGG    6780

AGTACTAAAG GGTCAAATAA CACTGAAGGA AGTGACACAA TCACCCTCCC ATGCAGAATA    6840

AAACAAATTA TAAACATGTG GCAGGAAGTA GGAAAAGCAA TGTATGCCCC TCCCATCAGT    6900

GGACAAATTA GATGTTCATC AAATATTACA GGGCTGCTAT TAACAAGAGA TGGTGGTAAT    6960

AGCAACAATG AGTCCGAGAT CTTCAGACCT GGAGGAGGAG ATATGAGGGA CAATTGGAGA    7020

AGTGAATTAT ATAAATATAA AGTAGTAAAA ATTGAACCAT TAGGAGTAGC ACCCACCAAG    7080

GCAAAGAGAA GAGTGGTGCA GAGAGAAAAA AGAGCAGTGG GAATAGGAGC TTTGTTCCTT    7140

GGGTTCTTGG GAGCAGCAGG AAGCACTATG GGCGCAGCGT CAATGACGCT GACGGTACAG    7200

GCCAGACAAT TATTGTCTGG TATAGTGCAG CAGCAGAACA ATTTGCTGAG GCTATTGAG     7260

GCGCAACAGC ATCTGTTGCA ACTCACAGTC TGGGGCATCA AGCAGCTCCA GGCAAGAATC    7320

CTGGCTGTGG AAAGATACCT AAAGGATCAA CAGCTCCTGG GGATTGGGG TTGCTCTGGA     7380

AAACTCATTT GCACCACTGC TGTGCCTTGG AATGCTAGTT GGAGTAATAA ATCTCTGGAA    7440
```

```
CAGATTTGGA ATAACATGAC CTGGATGGAG TGGGACAGAG AAATTAACAA TTACACAAGC    7500

TTAATACACT CCTTAATTGA AGAATCGCAA AACCAGCAAG AAAAGAATGA ACAAGAATTA    7560

TTGGAATTAG ATAAATGGGC AAGTTTGTGG AATTGGTTTA ACATAACAAA TTGGCTGTGG    7620

TATATAAAAT TATTCATAAT GATAGTAGGA GGCTTGGTAG GTTTAAGAAT AGTTTTTGCT    7680

GTACTTTCTG TAGTGAATAG AGTTAGGCAG GGATATTCAC CATTATCGTT TCAGACCCAC    7740

CTCCCAATCC CGAGGGGACC CGACAGGCCC GAAGGAATAG AAGAAGAAGG TGGAGAGAGA    7800

GACAGAGACA GATCCATTCG ATTAGTGAAC GGATCCTTAG CACTTATCTG GGACGATCTG    7860

CGGAGCCTGT GCCTCTTCAG CTACCACCGC TTGAGAGACT TACTCTTGAT TGTAACGAGG    7920

ATTGTGGAAC TTCTGGGACG CAGGGGGTGG GAAGCCCTCA AATATTGGTG GAATCTCCTA    7980

CAGTATTGGA GTCAGGAGCT AAAGAATAGT GCTGTTAGCT TGCTCAATGC CACAGCTATA    8040

GCAGTAGCTG AGGGGACAGA TAGGGTTATA GAAGTAGTAC AAGGAGCTTA TAGAGCTATT    8100

CGCCACATAC CTAGAAGAAT AAGACAGGGC TTGGAAAGGA TTTTGCTATA AGATGGGTGG    8160

CAAGTGGTCA AAAAGTAGTG TGGTTGGATG GCCTGCTGTA AGGGAAAGAA TGAGACGAGC    8220

TGAGCCAGCA GCAGATGGGG TGGGAGCAGC ATCTCGAGAC CTAGAAAAAC ATGGAGCAAT    8280

CACAAGTAGC AACACAGCAG CTAACAATGC TGATTGTGCC TGGCTAGAAG CACAAGAGGA    8340

GGAGGAGGTG GGTTTTCCAG TCACACCTCA GGTACCTTTA AGACCAATGA CTTACAAGGC    8400

AGCTGTAGAT CTTAGCCACT TTTTAAAAGA AAAGGGGGGA CTGGAAGGGC TAATTCACTC    8460

CCAACGAAGA CAAGATATCC TTGATCTGTG GATCTACCAC ACACAAGGCT ACTTCCCTGA    8520

TTAGCAGAAC TACACACCAG GGCCAGGGAT CAGATATCCA CTGACCTTTG GATGGTGCTA    8580

CAAGCTAGTA CCAGTTGAGC CAGAGAAGTT AGAAGAAGCC AACAAAGGAG AGAACACCAG    8640

CTTGTTACAC CCTGTGAGCC TGCATGGAAT GGATGACCCG GAGAGAGAAG TGTTAGAGTG    8700

GAGGTTTGAC AGCCGCCTAG CATTTCATCA CATGGCCCGA GAGCTGCATC CGGAGTACTT    8760

CAAGAACTGC TGACATCGAG CTTGCTACAA GGGACTTTCC GCTGGGGACT TTCCAGGGAG    8820

GCGTGGCCTG GGCGGGACTG GGGAGTGGCG AGCCCTCAGA TCCTGCATAT AAGCAGCTGC    8880

TTTTTGCCTG TACTGGGTCT CTCTGGTTAG ACCAGATCTG AGCCTGGGAG CTC           8933
```

(2) INFORMATION FOR SEQ ID NO:5:

(i) SEQUENCE CHARACTERISTICS:
        (A) LENGTH: 5362 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: HTLV-III (ix) FEATURE:
        (A) NAME/KEY: misc_feature
        (B) LOCATION: 1..5362
        (D) OTHER INFORMATION: /standard_name= "Clone BH5"
           /note= "Corresponds to nucleotide positions 222 to
           5585 in figure 3 of US 06/693,866 (parent)"

(xi) SEQUENCE DESCRIPTION: SEQ ID NO:5:

```
GAGCTCTCTC GACGCAGGAC TCGGCTTGCG AGCGCGCACG GCAAGAGGCG AGGGGCGGCG     60

ACTGGTGAGT ACGCCAAAAA TTTTGACTAG CGGAGGCTAG AAGGAGAGAG ATGGGTGCGA    120
```

```
GAGCGTCAGT ATTAAGCGGG GGAGAATTAG ATCGATGGGA AAAAATTCGG TTAAGGCCAG      180

GGGGAAAGAA AAAATATAAA TTAAAACATA TAGTATGGGC AAGCAGGGAG CTAGAACGAT      240

TCGCAGTTAA TCCTGGCCTG TTAGAAACAT CAGAAGGCTG TAGACAAATA CTGGACAGC       300

TACAACCATC CCTTCAGACA GGATCAGAAG AACTTAGATC ATTATATAAT ACAGTAGCAA      360

CCCTCTATTG TGTGCATCAA AGGATAGAGA TAAAAGACAC CAAGGAAGCT TTAGACAAGA      420

TAGAGGAAGA GCAAAACAAA AGTAAGAAAA AAGCACAGCA AGCAGCAGCT GACACAGGAC      480

ACAGCAGTCA GGTCAGCCAA AATTACCCTA TAGTGCAGAA CATCCAGGGG CAAATGGTAC      540

ATCAGGCCAT ATCACCTAGA ACTTTAAATG CATGGGTAAA AGTAGTAGAA GAGAAGGCTT      600

TCAGCCCAGA AGTGATACCC ATGTTTTCAG CATTATCAGA AGGAGCCACC CCACAAGATT      660

TAAACACCAT GCTAAACACA GTGGGGGGAC ATCAAGCAGC CATGCAAATG TTAAAGAGA       720

CCATCAATGA GGAAGCTGCA GAATGGGATA GAGTGCATCC AGTGCATGCA GGGCCTATCG      780

CACCAGGCCA GATGAGAGAA CCAAGGGGAA GTGACATAGC AGGAACTACT AGTACCCTTC      840

AGGAACAAAT AGGATGGATG ACAAATAATC CACCTATCCC AGTAGGAGAA ATTTATAAAA      900

GATGGATAAT CCTGGGATTA AATAAAATAG TAAGGATGTA TAGTCCTACC AGCATTCTGG      960

ACATAAGACA AGGACCAAAG GAACCCTTTA GAGACTATGT AGACCGGTTC TATAAAACTC     1020

TAAGAGCCGA GCAAGCTTCA CAGGAAGTAA AAAATTGGAT GACAGAAACC TTGTTGGTCC     1080

AAAATGCGAA CCCAGATTGT AAGACTATTT TAAAAGCATT GGGACCAGCG GCTACACTAG     1140

AAGAAATGAT GACAGCATGT CAGGGAGTAG GAGGACCCGG CCATAAGGCA AGAGTTTTGG     1200

CTGAAGCAAT GAGCCAAGTA ACAAATTCAA CTACCATAAT GATGCAAAGA GGCAATTTTA     1260

GGAACCAAAG AAAAATTGTT AAGTGTTTCA ATTGTGGCAA AGAAGGGCAC ATAGCAAGAA     1320

ATTGCAAGGC CCCTAGAAAA AAGGGCTGTT GGAAATGTGG AAAGGAAGGA CACCAAATGA     1380

AAGATTGTAC TGAGAGACAG GCTAATTTTT TAGGGAAGAT CTGGCCTTCC TACAAGGGAA     1440

GGCCAGGGAA TTTTCTTCAG AGCAGACCAG AGCCAACAGC CCCACCATTT CTTCAGAGCA     1500

GACCAGAGCC AACAGCCCCA CCAGAAGAGA GCTTCAGGTC TGGGGTAGAG ACAACAACTC     1560

CCCCTCAGAA GCAGGAGCCG ATAGACAAGG AACTGTATCC TTTAACTTCC CTCAGATCAC     1620

TCTTTGGCAA CGACCCCTCG TCACAATAAA GATAGGGGGG CAACTAAAGG AAGCTCTATT     1680

AGATACAGGA GCAGATGATA CAGTATTAGA AGAAATGAGT TTGCCAGGAA GATGGAAACC     1740

AAAAATGATA GGGGGAATTG GAGGTTTTAT CAAAGTAAGA CAGTATGATC AGATACTCAT     1800

AGAAATCTGT GGACATAAAG CTATAGGTAC AGTATTAGTA GGACCTACAC CTGTCAACAT     1860

AATTGGAAGA AATCTGTTGA CTCAGATTGG TTGCACTTTA AATTTTCCCA TTAGTCCTAT     1920

TGAAACTGTA CCAGTAAAAT TAAAGCCAGG AATGGATGGC CCAAAAGTTA AACAATGGCC     1980

ATTGACAGAA GAAAAAATAA AAGCATTAGT AGAAATTTGT ACAGAAATGG AAAAGGAAGG     2040

GAAAATTTCA AAAATTGGGC CTGAAAATCC ATACAATACT CCAGTATTTG CCATAAAGAA     2100

AAAAGACAGT ACTAAATGGA GAAAATTAGT AGATTTCAGA GAACTTAATA GGAGAACTCA     2160

AGACTTCTGG GAAGTTCAAT TGGGAATACC ACATCCCGCA GGGTTAAAAA AGAAAAAATC     2220

AGTAACAGTA CTGGATGTGG GTGATGCATA TTTTTCAGTT CCCTTAGATG AAGACTTCAG     2280

GAAGTATACT GCATTTACCA TACCTAGTAT AAATAATGAG ACACCAGGGA GTGGATATCA     2340

GTACAATGTG CTTCCACAGG GATGGAAAGG ATCACCAGCA ATATTCCAAA GTAGCATGAC     2400

AAAAATCTTA GAGCCTTTTA GAAAACAAAA TCCAGACATA GTTATTTATC AATACATGGA     2460

TGATTTGTAT GTAGGATCTG ACTTAGAAAT AGGGCAGCAT AGAACAAAAA TAGAGGAGCT     2520
```

```
GAGACAACAT CTGTTGAGGT GGGGATTTAC CACACCAGAC AAAAAACATC AGAAAGAACC    2580

TCCATTCCTT TGGATGGGTT ATGAACTCCA TCCTGATAAA TGGACGATAC AGCCTATAGT    2640

GCTGCCAGAA AAAGACAGCT GGACTGTCAA TGACATACAG AAGTTAGTGG GAAAATTGAA    2700

TTGGGCAAGT CAGATTTATC CAGGGATTAA AGTAAGGCAA TTATGTAAAC TCCTTAGAGG    2760

AACCAAAGCA CTAACAGAAG TAATACCACT AACAGAAGAA GCAGAGCTAG AACTGGCAGA    2820

AAACAGAGAG ATTCTAAAAG AACCAGTACA TGGAGTGTAT TATGACCCAT CAAAAGACTT    2880

AATAGCAGAA ATACAGAAGC AGGGGCAAGG CCAATGGACA TATCAAATTT ATCAAGAGCC    2940

ATTTAAAAAT CTGAAAACAG GAAAATATGC AAGAATGAGG GGTGCCCACA CTAATGATGT    3000

AAAACAATTA ACAGAGGCAG TGCAAAAAAT AACCACAGAA AGCATAGTAA TATGGGGAAA    3060

GACTCCTAAA TTTAAACTAC CCATACAAAA AGAAACATGG GAAACATGGT GGACAGAGTA    3120

TTGGCAAGCC ACCTGGATTC CTGAGTGGGA GTTTGTTAAT ACCCCTCCTT TAGTGAAATT    3180

ATGGTACCAG TTAGAGAAAG AACCCATAGT AGGAGCAGAA ACCTTCTATG TAGATGGGGC    3240

AGCTAGCAGG GAGACTAAAT TAGGAAAAGC AGGATATGTT ACTAATAGAG GAAGACAAAA    3300

AGTTGTCACC CTAACTCACA CAACAAATCA GAAGACTGAA TTACAAGCAA TTCATCTAGC    3360

TTTGCAGGAT TCGGGATTAG AAGTAAATAT AGTAACAGAC TCACAATATG CATTAGGAAT    3420

CATTCAAGCA CAACCAGATA AAAGTGAATC AGAGTTAGTC AATCAAATAA TAGAGCAGTT    3480

AATAAAAAAG GAAAAGGTCT ATCTGGCATG GGTACCAGCA CACAAAGGAA TTGGAGGAAA    3540

TGAACAAGTA GATAAATTAG TCAGTGCTGG AATCAGGAAA ATACTATTTT TAGATGGAAT    3600

AGATAAGGCC CAAGAAGAAC ATGAGAAATA TCACAGTAAT TGGAGAGCAA TGGCTAGTGA    3660

TTTTAACCTG CCACCTGTAG TAGCAAAAGA AATAGTAGCC AGCTGTGATA AATGTCAGCT    3720

AAAAGGAGAA GCCATGCATG GACAAGTAGA CTGTAGTCCA GGAATATGGC AACTAGATTG    3780

TACACATTTA GAAGGAAAAG TTATCCTGGT AGCAGTTCAT GTAGCCAGTG GATATATAGA    3840

AGCAGAAGTT ATTCCAGCAG AAACAGGGCA GGAAACAGCA TATTTTCTTT TAAAATTAGC    3900

AGGAAGATGG CCAGTAAAAA CAATACATAC AGACAATGGC AGCAATTTCA CCAGTGCTAC    3960

GGTTAAGGCC GCCTGTTGGT GGGCGGGAAT CAAGCAGGAA TTTGGAATTC CCTACAATCC    4020

CCAAAGTCAA GGAGTAGTAG AATCTATGAA TAAAGAATTA AGAAAAATTA TAGGACAGGT    4080

AAGAGATCAG GCTGAACATC TTAAGACAGC AGTACAAATG GCAGTATTCA TCCACAATTT    4140

TAAAAGAAAA GGGGGGATTG GGGGGTACAG TGCAGGGGAA AGAATAGTAG ACATAATAGC    4200

AACAGACATA CAAACTAAAG AATTACAAAA ACAAATTACA AAAATTCAAA ATTTTCGGGT    4260

TTATTACAGG GACAGCAGAA ATCCACTTTG GAAAGGACCA GCAAAGCTCC TCTGGAAAGG    4320

TGAAGGGGCA GTAGTAATAC AAGATAATAG TGACATAAAA GTAGTGCCAA GAAGAAAAGC    4380

AAAGATCATT AGGGATTATG GAAAACAGAT GGCAGGTGAT GATTGTGTGG CAAGTAGACA    4440

GGATGAGGAT TAGAACATGG AAAAGTTTAG TAAAACACCG TATGTATGTT TCAGGGAAAG    4500

CTAGGGGATG GTTTTATAGA CATCACTATG AAAGCCCTCA TCCAAGAATA AGTTCAGAAG    4560

TACACATCCC ACTAGGGGAT GCTAGATTGG TAATAACAAC ATATTGGGGT CTGCATACAG    4620

GAGAAAGAGA CTGGCATTTG GGTCAGGGAG TCTCCATAGA ATGGAGGAAA AGGAGATATA    4680

GCACACAAGT AGACCCTGAA CTAGCAGACC AACTAATTCA TCTGCATTAC TTTGATTGTT    4740

TTTCAGACTC TGCTATAAGA AAGGCCTTAT TAGGACACAT AGTTAGCCCT AGGTGTGAAT    4800

ATCAAGCAGG ACATAACAAG GTAGGATCTC TACAATACTT GGCACTAGCA GCATTAATAA    4860
```

```
CACCAAAAAA GGTAAAGCCA CCTTTGCCTA GTGTTACGAA ACTGACAGAG GATAGATGGA      4920

ACAAGCCCCA GAAGACCAAG GGCCACAGAG GAAGCCACAC AATGAATGGA CACTAGAGCT      4980

TTTAGAGGAG CTTAAGAATG AAGCTGTTAG ACATTTTCCT AGGATTTGGC TCCATGGCTT      5040

AGGGCAACAT ATCTATGAAA CTTATGGGGA TACTTGGGCA GGAGTGGAAG CCATAATAAG      5100

AATTCTGCAA CAACTGCTGT TTATCCATTT TCAGAATTGG GTGTCGACAT AGCAGAATAG      5160

GCGTTACTCA ACAGAGGAGA GCAAGAAATG GAGCCAGTAG ATCCTAGACT AGAGCCCTGG      5220

AAGCATCCAG GAAGTCAGCC TAAAACTGCT TGTACCACTT GCTATTGTAA AAAGTGTTGC      5280

TTTCATTGCC AAGTTTGTTT CATAACAAAA GCCTTAGGCA TCTCCTATGG CAGGAAGAAG      5340

CGGAGACAGC GACGAAGAGC TC                                              5362
```

(2) INFORMATION FOR SEQ ID NO:6:

(i) SEQUENCE CHARACTERISTICS:
        (A) LENGTH: 3563 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: HTLV-III (ix) FEATURE:
        (A) NAME/KEY: misc_feature
        (B) LOCATION: 1..3563
        (D) OTHER INFORMATION: /standard_name= "Clone BH8"
            /note= "Corresponds to nucleotide positions 5580
            to 9154 in figure 3 of US 06/693,866"

(xi) SEQUENCE DESCRIPTION: SEQ ID NO:6:

```
GAGCTCATCG AAGCAGTCAG ACTCATCAAG TTTCTCTATC AAAGCAGTAA GTAGTACATG        60

TAACGCAACC TATACCAATA GTAACAATAG TAGCCTTAGC AGTAGCAATA ATAATAGCAA       120

TAGTTGTGTG GTCCATAGTA ATCATAGAAT ATAGGAAAAT ATTAAGACAA AGAAAAATAG       180

ACAGGTTAAT TGATAGACTA ATAGAAAGAG CAGAAGACAG TGGCAATGAG AGTGAAGGAG       240

AAATATCAGC ACTTGTGGAG ATGGGGGTGG AGATGGGGCA CCATGCTCCT TGGGATGTTG       300

ATGATCTGTA GTGCTACAGA AAAATTGTGG GTCACAGTCT ATTTTGGGGT ACCTGTGTGG       360

AAGGAAGCAA CCACCACTCT ATTTTGTGCA TCAGATGCTA AAGCATATGA TACAGAGGTA       420

CATAATGTTT GGGCCACACA TGCCTGTGTA CCCACAGACC CCAACCCACA AGAAGTAGTA       480

TTGGTAAATG TGACAGAAAA TTTTAACATG TGGAAAAATG ACATGGTAGA ACAGATGCAT       540

GAGGATATAA TCAGTTTATG GGATCAAAGC CTAAAGCCAT GTGTAAAATT AACCCCACTC       600

TGTGTTAGTT TAAAGTGCAC TGATTTGAAG AATGATACTA ATACCAATAG TAGTAGCGGG       660

AGAATGATAA TGGAGAAAGG AGAGATAAAA AACTGCTCTT TCAATATCAG CACAAGCAAA       720

AGAGGTAAGG TGCAGAAAGA ATATGCATTT TTTTATAAAC TTGATATAAT ACCAATAGAT       780

AATGATACTA CCAGCTATAC GTTGACAAGT TGTAACACCT CAGTCATTAC ACAGGCCTGT       840

CCAAAGGTAT CCTTTGAGCC AATTCCCATA CATTATTGTG CCCCGGCTGG TTTTGCGATT       900

CTAAAATGTA ATAATAAGAC GTTCAATGGA ACAGGACCAT GTACAAATGT CAGCACAGTA       960

CAATGTACAC ATGGAATTAG GCCAGTAGTA TCAACTCAAC TGCTGTTAAA TGGCAGTCTG      1020

GCAGAAGAAG AGGTAGTAAT TAGATCTGTC AATTTCACGG ACAATGCTAA AACCATAATA      1080
```

```
                                                    -continued

GTACAGCTGG ACACATCTGT AGAAATTAAT TGTACAAGAC CCAACAACAA TACAAGAAAA    1140

AAAATCCGTA TCCAGAGGGG ACCAGGGAGA GCATTTGTTA CAATAGGAAA AATAGGAAAT    1200

ATGAGACAAG CACATTGTAA CATTAGTAGA GCAAAATGGA ATGCCACTTT AAAACAGATA    1260

GATAGCAAAT TAAGAGAACA ATTTGGAAAT AATAAAACAA TAATCTTTAA GCAGTCCTCA    1320

GGAGGGGACC CAGAAATTGT AACGCACAGT TTTAATTGTG GAGGGGAATT TTTCTACTGT    1380

AATTCAACAC AACTGTTTAA TAGTACTTGG AGTACTAAAG GGTCAAATAA CACTGAAGGA    1440

AGTGACACAA TCACCCTCCC ATGCAGAATA AAACAAATTA TAAACATGTG GCAGGAAGTA    1500

GGAAAAGCAA TGTATGCCCC TCCCATCAGT GGACAAATTA GATGTTCATC AAATATTACA    1560

GGGCTGCTAT TAACAAGAGA TGGTGGTAAT AGCAACAATG AGTCCGAGAT CTTCAGACCT    1620

GGAGGAGGAG ATATGAGGGA CAATTGGAGA AGTGAATTAT ATAAATATAA AGTAGTAAAA    1680

ATTGAACCAT TAGGAGTAGC ACCCACCAAG GCAAAGAGAA GAGTGGTGCA GAGAGAAAAA    1740

AGAGCAGTGG GAATAGGAGC TTTGTTCCTT GGGTTCTTGG GAGCAGCAGG AAGCACTATG    1800

GGCGCAGCGT CAATGACGCT GACGGTACAG GCCAGACAAT TATTGTCTGG TATAGTGCAG    1860

CAGCAGAACA ATTTGCTGAG GGCTATTGAG GGCCAACAGC ATCTGTTGCA ACTCACAGTC    1920

TGGGGCATCA AGCAGCTCCA GGCAAGAATC CTGGCTGTGG AAAGATACCT AAAGGATCAA    1980

CAGCTCCTGG GGATTTGGGG TTGCTCTGGA AAACTCATTT GCACCACTGC TGTGCCTTGG    2040

AATGCTAGTT GGAGTAATAA ATCTCTGGAA CAGATTTGGA ATAACATGAC CTGGATGGAG    2100

TGGGACAGAG AAAATTAACAA TTACACAAGC TTAATACACT CCTTAATTGA AGAATCGCAA    2160
```

-continued

```
AGCCCTCAGA TCCTGCATAT AAGCAGCTGC TTTTTGCCTG TACTGGGTCT CTCTGGTTAG    3540

ACCAGATCTG AGCCTGGGAG CTC                                            3563
```

(2) INFORMATION FOR SEQ ID NO:7:

(i) SEQUENCE CHARACTERISTICS:
        (A) LENGTH: 142 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: HTLV-III (ix) FEATURE:
        (A) NAME/KEY: misc_feature
        (B) LOCATION: 1..142
        (D) OTHER INFORMATION: /standard_name= "Clone HXB2"
            /note= "Corresponds to nucleotide positions 9155
            to 9296 in figure 3 of US 06/693,866"

(xi) SEQUENCE DESCRIPTION: SEQ ID NO:7:

```
TCTGGCTAGC TAGGGAACCC ACTGCTTAAG CCTCAATAAA GCTTGCCTTG AGTGCTTCAA      60

GTAGTGTGTG CCCGTCTGTT GTGTGACTCT GGTAACTAGA GATCCCTCAG ACCCTTTTAG     120

TCAGTGTGGA AAATCTCTAG CA                                              142
```

(2) INFORMATION FOR SEQ ID NO:8:

(i) SEQUENCE CHARACTERISTICS:
        (A) LENGTH: 512 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: HTLV-III (ix) FEATURE:
        (A) NAME/KEY: Protein
        (B) LOCATION: 1..512
        (D) OTHER INFORMATION: /note= "gag protein of HTLV-III"

(xi) SEQUENCE DESCRIPTION: SEQ ID NO:8:

```
Met Gly Ala Arg Ala Ser Val Leu Ser Gly Gly Glu Leu Asp Arg Trp
1               5                  10                  15

Glu Lys Ile Arg Leu Arg Pro Gly Gly Lys Lys Tyr Lys Leu Lys
            20                  25                  30

His Ile Val Trp Ala Ser Arg Glu Leu Glu Arg Phe Ala Val Asn Pro
            35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Asp Lys Ile Glu Glu Glu Gln Asn Lys Ser Lys
            100                 105                 110
```

```
Lys Lys Ala Gln Gln Ala Ala Asp Thr Gly His Ser Ser Gln Val
        115                 120                 125
Ser Gln Asn Tyr Pro Ile Val Gln Asn Ile Gln Gly Gln Met Val His
    130                 135                 140
Gln Ala Ile Ser Pro Arg Thr Leu Asn Ala Trp Val Lys Val Val Glu
145                 150                 155                 160
Glu Lys Ala Phe Ser Pro Glu Val Ile Pro Met Phe Ser Ala Leu Ser
                165                 170                 175
Glu Gly Ala Thr Pro Gln Asp Leu Asn Thr Met Leu Asn Thr Val Gly
            180                 185                 190
Gly His Gln Ala Ala Met Gln Met Leu Lys Glu Thr Ile Asn Glu Glu
        195                 200                 205
Ala Ala Glu Trp Asp Arg Val His Pro Val His Ala Gly Pro Ile Ala
    210                 215                 220
Pro Gly Gln Met Arg Glu Pro Arg Gly Ser Asp Ile Ala Gly Thr Thr
225                 230                 235                 240
Ser Thr Leu Gln Glu Gln Ile Gly Trp Met Thr Asn Asn Pro Pro Ile
                245                 250                 255
Pro Val Gly Glu Ile Tyr Lys Arg Trp Ile Ile Leu Gly Leu Asn Lys
            260                 265                 270
Ile Val Arg Met Tyr Ser Pro Thr Ser Ile Leu Asp Ile Arg Gln Gly
        275                 280                 285
Pro Lys Glu Pro Phe Arg Asp Tyr Val Asp Arg Phe Tyr Lys Thr Leu
    290                 295                 300
Arg Ala Glu Gln Ala Ser Gln Glu Val Lys Asn Trp Met Thr Glu Thr
305                 310                 315                 320
Leu Leu Val Gln Asn Ala Asn Pro Asp Cys Lys Thr Ile Leu Lys Ala
                325                 330                 335
Leu Gly Pro Ala Ala Thr Leu Glu Glu Met Met Thr Ala Cys Gln Gly
            340                 345                 350
Val Gly Gly Pro Gly His Lys Ala Arg Val Leu Ala Glu Ala Met Ser
        355                 360                 365
Gln Val Thr Asn Thr Ala Thr Ile Met Met Gln Arg Gly Asn Phe Arg
    370                 375                 380
Asn Gln Arg Lys Met Val Lys Cys Phe Asn Cys Gly Lys Glu Gly His
385                 390                 395                 400
Thr Ala Arg Asn Cys Arg Ala Pro Arg Lys Lys Gly Cys Trp Lys Cys
                405                 410                 415
Gly Lys Glu Gly His Gln Met Lys Asp Cys Thr Glu Arg Gln Ala Asn
            420                 425                 430
Phe Leu Gly Lys Ile Trp Pro Ser Tyr Lys Gly Arg Pro Gly Asn Phe
        435                 440                 445
Leu Gln Ser Arg Pro Glu Pro Thr Ala Pro Pro Phe Leu Gln Ser Arg
    450                 455                 460
Pro Glu Pro Thr Ala Pro Pro Glu Glu Ser Phe Arg Ser Gly Val Glu
465                 470                 475                 480
Thr Thr Thr Pro Pro Gln Lys Gln Glu Pro Ile Asp Lys Glu Leu Tyr
                485                 490                 495
Pro Leu Thr Ser Leu Arg Ser Leu Phe Gly Asn Asp Pro Ser Ser Gln
            500                 505                 510

(2) INFORMATION FOR SEQ ID NO:9:
```

```
    (i) SEQUENCE CHARACTERISTICS:
        (A) LENGTH: 1015 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: HTLV-III (ix) FEATURE:
        (A) NAME/KEY: Protein
        (B) LOCATION: 1..1015
        (D) OTHER INFORMATION: /note= "pol protein of HTLV-III"

(xi) SEQUENCE DESCRIPTION: SEQ ID NO:9:

Phe Phe Arg Glu Asp Leu Ala Phe Leu Gln Gly Lys Ala Arg Glu Phe
1               5                   10                  15

Ser Ser Glu Gln Thr Arg Ala Asn Ser Pro Thr Ile Ser Ser Glu Gln
            20                  25                  30

Thr Arg Ala Asn Ser Pro Thr Arg Arg Glu Leu Gln Val Trp Gly Arg
        35                  40                  45

Asp Asn Asn Ser Pro Ser Glu Ala Gly Ala Asp Arg Gln Gly Thr Val
50                  55                  60

Ser Phe Asn Phe Pro Gln Ile Thr Leu Trp Gln Arg Pro Leu Val Thr
65                  70                  75                  80

Ile Lys Ile Gly Gly Gln Leu Lys Glu Ala Leu Leu Asp Thr Gly Ala
                85                  90                  95

Asp Asp Thr Val Leu Glu Glu Met Ser Leu Pro Gly Arg Trp Lys Pro
            100                 105                 110

Lys Met Ile Gly Gly Ile Gly Gly Phe Ile Lys Val Arg Gln Tyr Asp
        115                 120                 125

Gln Ile Leu Ile Glu Ile Cys Gly His Lys Ala Ile Gly Thr Val Leu
130                 135                 140

Val Gly Pro Thr Pro Val Asn Ile Ile Gly Arg Asn Leu Leu Thr Gln
145                 150                 155                 160

Ile Gly Cys Thr Leu Asn Phe Pro Ile Ser Pro Ile Glu Thr Val Pro
                165                 170                 175

Val Lys Leu Lys Pro Gly Met Asp Gly Pro Lys Val Lys Gln Trp Pro
            180                 185                 190

Leu Thr Glu Glu Lys Ile Lys Ala Leu Val Glu Ile Cys Thr Glu Met
        195                 200                 205

Glu Lys Glu Gly Lys Ile Ser Lys Ile Gly Pro Glu Asn Pro Tyr Asn
210                 215                 220

Thr Pro Val Phe Ala Ile Lys Lys Asp Ser Thr Lys Trp Arg Lys
225                 230                 235                 240

Leu Val Asp Phe Arg Glu Leu Asn Lys Arg Thr Gln Asp Phe Trp Glu
                245                 250                 255

Val Gln Leu Gly Ile Pro His Pro Ala Gly Leu Lys Lys Lys Lys Ser
            260                 265                 270

Val Thr Val Leu Asp Val Gly Asp Ala Tyr Phe Ser Val Pro Leu Asp
        275                 280                 285

Glu Asp Phe Arg Lys Tyr Thr Ala Phe Thr Ile Pro Ser Ile Asn Asn
290                 295                 300

Glu Thr Pro Gly Ile Arg Tyr Gln Tyr Asn Val Leu Pro Gln Gly Trp
305                 310                 315                 320
```

-continued

Lys Gly Ser Pro Ala Ile Phe Gln Ser Ser Met Thr Lys Ile Leu Glu
            325                 330                 335

Pro Phe Lys Lys Gln Asn Pro Asp Ile Val Ile Tyr Gln Tyr Met Asp
            340                 345                 350

Asp Leu Tyr Val Gly Ser Asp Leu Glu Ile Gly Gln His Arg Thr Lys
            355                 360                 365

Ile Glu Glu Leu Arg Gln His Leu Leu Arg Trp Gly Leu Thr Thr Pro
    370                 375                 380

Asp Lys Lys His Gln Lys Glu Pro Pro Phe Leu Trp Met Gly Tyr Glu
385                 390                 395                 400

Leu His Pro Asp Lys Trp Thr Val Gln Pro Ile Val Leu Pro Glu Lys
                405                 410                 415

Asp Ser Trp Thr Val Asn Asp Ile Gln Lys Leu Val Gly Lys Leu Asn
                420                 425                 430

Trp Ala Ser Gln Ile Tyr Pro Gly Ile Lys Val Arg Gln Leu Cys Lys
            435                 440                 445

Leu Leu Arg Gly Thr Lys Ala Leu Thr Glu Val Ile Pro Leu Thr Glu
    450                 455                 460

Glu Ala Glu Leu Glu Leu Ala Glu Asn Arg Glu Ile Leu Lys Glu Pro
465                 470                 475                 480

Val His Gly Val Tyr Tyr Asp Pro Ser Lys Asp Leu Ile Ala Glu Ile
                485                 490                 495

Gln Lys Gln Gly Gln Gly Gln Trp Thr Tyr Gln Ile Tyr Gln Glu Pro
            500                 505                 510

Phe Lys Asn Leu Lys Thr Gly Lys Tyr Ala Arg Met Arg Gly Ala His
            515                 520                 525

Thr Asn Asp Val Lys Gln Leu Thr Glu Ala Val Gln Lys Ile Thr Thr
    530                 535                 540

Glu Ser Ile Val Ile Trp Gly Lys Thr Pro Lys Phe Lys Leu Pro Ile
545                 550                 555                 560

Gln Lys Glu Thr Trp Glu Thr Trp Trp Thr Glu Tyr Trp Gln Ala Thr
                565                 570                 575

Trp Ile Pro Glu Trp Glu Phe Val Asn Thr Pro Pro Leu Val Lys Leu
            580                 585                 590

Trp Tyr Gln Leu Glu Lys Glu Pro Ile Val Gly Ala Glu Thr Phe Tyr
            595                 600                 605

Val Asp Gly Ala Ala Asn Arg Glu Thr Lys Leu Gly Lys Ala Gly Tyr
    610                 615                 620

Val Thr Asn Lys Gly Arg Gln Lys Val Val Pro Leu Thr Asn Thr Thr
625                 630                 635                 640

Asn Gln Lys Thr Glu Leu Gln Ala Ile Tyr Leu Ala Leu Gln Asp Ser
                645                 650                 655

Gly Leu Glu Val Asn Ile Val Thr Asp Ser Gln Tyr Ala Leu Gly Ile
            660                 665                 670

Ile Gln Ala Gln Pro Asp Lys Ser Glu Ser Glu Leu Val Asn Gln Ile
            675                 680                 685

Ile Glu Gln Leu Ile Lys Lys Glu Lys Val Tyr Leu Ala Trp Val Pro
    690                 695                 700

Ala His Lys Gly Ile Gly Gly Asn Glu Gln Val Asp Lys Leu Val Ser
705                 710                 715                 720

Ala Gly Ile Arg Lys Ile Leu Phe Leu Asp Gly Ile Asp Lys Ala Gln
                725                 730                 735

```
Asp Glu His Glu Lys Tyr His Ser Asn Trp Arg Ala Met Ala Ser Asp
                740                 745                 750

Phe Asn Leu Pro Pro Val Val Ala Lys Glu Ile Val Ala Ser Cys Asp
                755                 760                 765

Lys Cys Gln Leu Lys Gly Glu Ala Met His Gly Gln Val Asp Cys Ser
            770                 775                 780

Pro Gly Ile Trp Gln Leu Asp Cys Thr His Leu Glu Gly Lys Val Ile
785                 790                 795                 800

Leu Val Ala Val His Val Ala Ser Gly Tyr Ile Glu Ala Glu Val Ile
                805                 810                 815

Pro Ala Glu Thr Gly Gln Glu Thr Ala Tyr Phe Leu Leu Lys Leu Ala
                820                 825                 830

Gly Arg Trp Pro Val Lys Thr Ile His Thr Asp Asn Gly Ser Asn Phe
            835                 840                 845

Thr Ser Ala Thr Val Lys Ala Ala Cys Trp Trp Ala Gly Ile Lys Gln
850                 855                 860

Glu Phe Gly Ile Pro Tyr Asn Pro Gln Ser Gln Gly Val Val Glu Ser
865                 870                 875                 880

Met Asn Lys Glu Leu Lys Lys Ile Ile Gly Gln Val Arg Asp Gln Ala
                885                 890                 895

Glu His Leu Lys Thr Ala Val Gln Met Ala Val Phe Ile His Asn Phe
                900                 905                 910

Lys Arg Lys Gly Gly Ile Gly Gly Tyr Ser Ala Gly Glu Arg Ile Val
            915                 920                 925

Asp Ile Ile Ala Thr Asp Ile Gln Thr Lys Glu Leu Gln Lys Gln Ile
930                 935                 940

Thr Lys Ile Gln Asn Phe Arg Val Tyr Tyr Arg Asp Ser Arg Asn Pro
945                 950                 955                 960

Leu Trp Lys Gly Pro Ala Lys Leu Leu Trp Lys Gly Glu Gly Ala Val
                965                 970                 975

Val Ile Gln Asp Asn Ser Asp Ile Lys Val Val Pro Arg Arg Lys Ala
                980                 985                 990

Lys Ile Ile Arg Asp Tyr Gly Lys Gln Met Ala Gly Asp Asp Cys Val
            995                 1000                1005

Ala Ser Arg Gln Asp Glu Asp
        1010                1015

(2) INFORMATION FOR SEQ ID NO:10:

(i) SEQUENCE CHARACTERISTICS:
        (A) LENGTH: 203 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: HTLV-III (ix) FEATURE:
        (A) NAME/KEY: Protein
        (B) LOCATION: 1..203
        (D) OTHER INFORMATION: /note= "sor protein of HTLV-III"

(xi) SEQUENCE DESCRIPTION: SEQ ID NO:10:

Cys Gln Glu Glu Lys Gln Arg Ser Leu Gly Ile Met Glu Asn Arg Trp
1               5                   10                  15
```

-continued

```
Gln Val Met Ile Val Trp Gln Val Asp Arg Met Arg Ile Arg Thr Trp
            20                  25                  30
Lys Ser Leu Val Lys His His Met Tyr Val Ser Gly Lys Ala Arg Gly
        35                  40                  45
Trp Phe Tyr Arg His His Tyr Glu Ser Pro His Pro Arg Ile Ser Ser
    50                  55                  60
Glu Val His Ile Pro Leu Gly Asp Ala Arg Leu Val Ile Thr Thr Tyr
65                  70                  75                  80
Trp Gly Leu His Thr Gly Glu Arg Asp Trp His Leu Gly Gln Gly Val
                85                  90                  95
Ser Ile Glu Trp Arg Lys Lys Arg Tyr Ser Thr Gln Val Asp Pro Glu
            100                 105                 110
Leu Ala Asp Gln Leu Ile His Leu Tyr Tyr Phe Asp Cys Phe Ser Asp
        115                 120                 125
Ser Ala Ile Arg Lys Ala Leu Leu Gly His Ile Val Ser Pro Arg Cys
    130                 135                 140
Glu Tyr Gln Ala Gly His Asn Lys Val Gly Ser Leu Gln Tyr Leu Ala
145                 150                 155                 160
Leu Ala Ala Leu Ile Thr Pro Lys Lys Ile Lys Pro Pro Leu Pro Ser
                165                 170                 175
Val Thr Lys Leu Thr Glu Asp Arg Trp Asn Lys Pro Gln Lys Thr Lys
            180                 185                 190
Gly His Arg Gly Ser His Thr Met Asn Gly His
        195                 200

(2) INFORMATION FOR SEQ ID NO:11:

(i) SEQUENCE CHARACTERISTICS:
        (A) LENGTH: 863 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: HTLV-III (ix) FEATURE:
        (A) NAME/KEY: Protein
        (B) LOCATION: 1..863
        (D) OTHER INFORMATION: /note= "env protein of HTLV-III"

(xi) SEQUENCE DESCRIPTION: SEQ ID NO:11:

Lys Glu Gln Lys Thr Val Ala Met Arg Val Lys Glu Lys Tyr Gln His
1               5                   10                  15
Leu Trp Arg Trp Gly Trp Arg Trp Gly Thr Met Leu Leu Gly Met Leu
            20                  25                  30
Met Ile Cys Ser Ala Thr Glu Lys Leu Trp Val Thr Val Tyr Tyr Gly
        35                  40                  45
Val Pro Val Trp Lys Glu Ala Thr Thr Thr Leu Phe Cys Ala Ser Asp
    50                  55                  60
Ala Lys Ala Tyr Asp Thr Glu Val His Asn Val Trp Ala Thr His Ala
65                  70                  75                  80
Cys Val Pro Thr Asp Pro Asn Pro Gln Glu Val Val Leu Val Asn Val
                85                  90                  95
Thr Glu Asn Phe Asn Met Trp Lys Asn Asp Met Val Glu Gln Met His
```

```
                100                 105                 110
Glu Asp Ile Ile Ser Leu Trp Asp Gln Ser Leu Lys Pro Cys Val Lys
            115                 120                 125
Leu Thr Pro Leu Cys Val Ser Leu Lys Cys Thr Asp Leu Lys Asn Asp
130                 135                 140
Thr Asn Thr Asn Ser Ser Ser Gly Arg Met Ile Met Glu Lys Gly Glu
145                 150                 155                 160
Ile Lys Asn Cys Ser Phe Asn Ile Ser Thr Ser Ile Arg Gly Lys Val
                165                 170                 175
Gln Lys Glu Tyr Ala Phe Phe Tyr Lys Leu Asp Ile Ile Pro Ile Asp
            180                 185                 190
Asn Asp Thr Thr Ser Tyr Thr Leu Thr Ser Cys Asn Thr Ser Val Ile
            195                 200                 205
Thr Gln Ala Cys Pro Lys Val Ser Phe Glu Pro Ile Pro Ile His Tyr
        210                 215                 220
Cys Ala Pro Ala Gly Phe Ala Ile Leu Lys Cys Asn Asn Lys Thr Phe
225                 230                 235                 240
Asn Gly Thr Gly Pro Cys Thr Asn Val Ser Thr Val Gln Cys Thr His
                245                 250                 255
Gly Ile Arg Pro Val Val Ser Thr Gln Leu Leu Leu Asn Gly Ser Leu
            260                 265                 270
Ala Glu Glu Glu Val Val Ile Arg Ser Ala Asn Phe Thr Asp Asn Ala
        275                 280                 285
Lys Thr Ile Ile Val Gln Leu Asn Gln Ser Val Glu Ile Asn Cys Thr
        290                 295                 300
Arg Pro Asn Asn Asn Thr Arg Lys Ser Ile Arg Ile Gln Arg Gly Pro
305                 310                 315                 320
Gly Arg Ala Phe Val Thr Ile Gly Lys Ile Gly Asn Met Arg Gln Ala
                325                 330                 335
His Cys Asn Ile Ser Arg Ala Lys Trp Asn Asn Thr Leu Lys Gln Ile
                340                 345                 350
Asp Ser Lys Leu Arg Glu Gln Phe Gly Asn Asn Lys Thr Ile Ile Phe
        355                 360                 365
Lys Gln Ser Ser Gly Gly Asp Pro Glu Ile Val Thr His Ser Phe Asn
        370                 375                 380
Cys Gly Gly Glu Phe Phe Tyr Cys Asn Ser Thr Gln Leu Phe Asn Ser
385                 390                 395                 400
Thr Trp Phe Asn Ser Thr Trp Ser Thr Lys Gly Ser Asn Asn Thr Glu
                405                 410                 415
Gly Ser Asp Thr Ile Thr Leu Pro Cys Arg Ile Lys Gln Ile Ile Asn
                420                 425                 430
Met Trp Gln Glu Val Gly Lys Ala Met Tyr Ala Pro Pro Ile Ser Gly
            435                 440                 445
Gln Ile Arg Cys Ser Ser Asn Ile Thr Gly Leu Leu Leu Thr Arg Asp
        450                 455                 460
Gly Gly Asn Ser Asn Asn Glu Ser Glu Ile Phe Arg Pro Gly Gly Gly
465                 470                 475                 480
Asp Met Arg Asp Asn Trp Arg Ser Glu Leu Tyr Lys Tyr Lys Val Val
                485                 490                 495
Lys Ile Glu Pro Leu Gly Val Ala Pro Thr Lys Ala Lys Arg Arg Val
            500                 505                 510
Val Gln Arg Glu Lys Arg Ala Val Gly Ile Gly Ala Leu Phe Leu Gly
        515                 520                 525
```

-continued

```
Phe Leu Gly Ala Ala Gly Ser Thr Met Gly Ala Ala Ser Met Thr Leu
    530                 535                 540

Thr Val Gln Ala Arg Gln Leu Leu Ser Gly Ile Val Gln Gln Gln Asn
545                 550                 555                 560

Asn Leu Leu Arg Ala Ile Glu Ala Gln Gln His Leu Leu Gln Leu Thr
                565                 570                 575

Val Trp Gly Ile Lys Gln Leu Gln Ala Arg Ile Leu Ala Val Glu Arg
            580                 585                 590

Tyr Leu Lys Asp Gln Gln Leu Leu Gly Ile Trp Gly Cys Ser Gly Lys
        595                 600                 605

Leu Ile Cys Thr Thr Ala Val Pro Trp Asn Ala Ser Trp Ser Asn Lys
    610                 615                 620

Ser Leu Glu Gln Ile Trp Asn Asn Met Thr Trp Met Glu Trp Asp Arg
625                 630                 635                 640

Glu Ile Asn Asn Tyr Thr Ser Leu Ile His Ser Leu Ile Glu Glu Ser
                645                 650                 655

Gln Asn Gln Gln Glu Lys Asn Glu Gln Glu Leu Leu Glu Leu Asp Lys
            660                 665                 670

Trp Ala Ser Leu Trp Asn Trp Phe Asn Ile Thr Asn Trp Leu Trp Tyr
        675                 680                 685

Ile Lys Leu Phe Ile Met Ile Val Gly Gly Leu Val Gly Leu Arg Ile
    690                 695                 700

Val Phe Ala Val Leu Ser Val Val Asn Arg Val Arg Gln Gly Tyr Ser
705                 710                 715                 720

Pro Leu Ser Phe Gln Thr His Leu Pro Ile Pro Arg Gly Pro Asp Arg
                725                 730                 735

Pro Glu Gly Ile Glu Glu Glu Gly Gly Glu Arg Asp Arg Asp Arg Ser
            740                 745                 750

Ile Arg Leu Val Asn Gly Ser Leu Ala Leu Ile Trp Asp Asp Leu Arg
        755                 760                 765

Ser Leu Cys Leu Phe Ser Tyr His Arg Leu Arg Asp Leu Leu Leu Ile
    770                 775                 780

Val Thr Arg Ile Val Glu Leu Leu Gly Arg Arg Gly Trp Glu Ala Leu
785                 790                 795                 800

Lys Tyr Trp Trp Asn Leu Leu Gln Tyr Trp Ser Gln Glu Leu Lys Asn
                805                 810                 815

Ser Ala Val Ser Leu Leu Asn Ala Thr Ala Ile Ala Val Ala Glu Gly
            820                 825                 830

Thr Asp Arg Val Ile Glu Val Val Gln Gly Ala Tyr Arg Ala Ile Arg
        835                 840                 845

His Ile Pro Arg Arg Ile Arg Gln Gly Leu Glu Arg Ile Leu Leu
    850                 855                 860
```